(12) United States Patent
Primard-Brisset et al.

(10) Patent No.: US 7,812,217 B2
(45) Date of Patent: Oct. 12, 2010

(54) **METHOD OF PRODUCING DOUBLE LOW RESTORER LINES OF *BRASSICA NAPUS* HAVING A GOOD AGRONOMIC VALUE**

(75) Inventors: Catherine Primard-Brisset, Saint Remy les Chevreuse (FR); Régine Delourme, L'Hermittage (FR); Jean-Pierre Poupard, Versailles (FR); Nicolas Pierre Poupard, legal representative, Chilly-Mazarin (FR); Marion Hélène Poupard, legal representative, Long Jumeau (FR); Raymonde Horvais, Montreuil-sur-Ille (FR); Françoise Budar, Les Molieres (FR); Georges Pelletier, Bures sur Yvette (FR); Michel Renard, Le Rheu (FR)

(73) Assignee: Institut National de la Recherche Agronomique (FR)

( * ) Notice: Subject to any disclaimer, the term of this patent is extended or adjusted under 35 U.S.C. 154(b) by 745 days.

(21) Appl. No.: 10/563,277

(22) PCT Filed: Jul. 5, 2004

(86) PCT No.: PCT/IB2004/002491

§ 371 (c)(1),
(2), (4) Date: Jul. 13, 2006

(87) PCT Pub. No.: WO2005/002324

PCT Pub. Date: Jan. 13, 2005

(65) Prior Publication Data

US 2007/0256150 A1  Nov. 1, 2007

(30) Foreign Application Priority Data

Jul. 4, 2003 (EP) .................................. 03291677
Dec. 8, 2003 (EP) .................................. 03293057

(51) Int. Cl.
*C12N 15/10* (2006.01)
*C12N 15/29* (2006.01)
*A01H 1/02* (2006.01)

(52) U.S. Cl. ........................ 800/267; 800/274; 800/306

(58) Field of Classification Search ........................ None
See application file for complete search history.

(56) References Cited

OTHER PUBLICATIONS

Pellan-Delourme et al. Genome 30: 234-238 (1988).*

Primard-Brisset et al. Theoretical and Applied Genetics 11: 736-746 (2005).*
Bartkowiak-Broda et al. 1999. Proceedings of the 10th International Rapeseed Congress, Camberra, Australia, pp. 1-5.*
Delourme et al. 1999. Proceedings of the 10th International Rapeseed Congress, Camberra, Australia, pp. 6-9.*
Desloire et al., "Identification of the fertility restoration locus, *Rfo*, in radish, as a member of the pentatricopeptide-repeat protein family", EMBO reports vol. 4, No. 6, pp. 588-594, Jun. 6, 2003.
Delourme et al., Characterisation of the radish introgression carrying the *Rfo*, restorer gene for the *Ogu*-INRA cytoplasmic male sterility in rapeseed (*Brassica napus* I.), Theoretical and Applied Genetics, vol. 97, No. 1-2, pp. 129-134, Jul. 1998.
Delourme et al., Linkage between an isozyme marker and a restorer gene in radish cytoplasmic male sterility of rapeseed (*Brassica napus* L.), Theoretical and Applied Genetics, vol. 85, pp. 222-228, Springer, Berlin, DE, 1992.
Delourme et al., Identification of RAPD markers linked to a fertility restorer gene for the Ogura radish cytoplasmic male sterility of rapeseed (*Brassica napus* L.), Theoretical and Applied Genetics, vol. 88, No. 6/7, pp. 741-748, 1994, Springer, Berlin, DE.
Bellaoui et al., "The restorer *Rfo* gene acts post-translationally on the stability of the ORF138 CMS-associated protein in reproductive tissue of rapeseed cybrids", vol. 40, No. 5, pp. 893-902, Jul. 1999, Plant Molecular Biol, NIJHOFF publishers, Dordrecht, NL.
Giancola et al., "Characterization of a radish introgression carrying the Ogura fertility restorer gene *Rfo* in rapeseed, using the *Arabidopsis* genome sequence and radish genetic mapping", TAG. Theoretical and Applied Genetics.vol. 107, No. 8, pp. 1442-1451, Aug. 27, 2003 Germany.
Fourmann et al., "From *Arabidopsis thaliana* to *Brassica napus*: development of amplified consensus genetic markers (ACGM) for construction of a gene map", Theor . Appl. Genet, vol. 105, pp. 1196-1206, 2002.
Delourme et al., "Double Low Restored F1 Hybrids Can Be Produced With the Ogu-INRA CMS in Rapeseed", *10th* Rapeseed Congress, Canaberra 1999, (pp. 26-29).

* cited by examiner

*Primary Examiner*—David T Fox
(74) *Attorney, Agent, or Firm*—Lerner, David, Littenberg, Krumholz & Mentlik, LLP

(57) ABSTRACT

The invention relates to a method of producing a double low restorer line of *Brassica napus* for Ogura cytoplasmic male sterility (cms) presenting a radish introgression carrying the Rfo restorer gene deleted of the radish Pgi-2 allele and recombined with the Pgi-2 gene from *Brassica oleracea*, and having a good agronomic value characterized by female fertility, a good transmission rate of Rfo and a high vegetative vigour. The invention relates also to a method of forming *Brassica napus* hybrid seeds and progeny thereof and to the use of markers for selection.

1 Claim, 25 Drawing Sheets

Fig. 1: Seed set on 'R211' and 'R2000'

| Genotype | Selfings | Test Crosses |
|---|---|---|
| Drakkar | 29.3 | |
| Pactol | 23.1 | |
| R211 | 11.2 | 25.5 |
| R2000 | 26.5 (24.0 – 31.1) | 27.0 (24.0 – 28.7) |

```
                            51                         81 PGIo1 U  -->  100
consePGIinTUNTDrakka   ..........  ..........  ..........  ..........  ..........
      consensWesrPGI   ..........  ..........  ..........  ..........  ..........
   consePGIintUNTR113  ..........  ..........  ..........  ..........  ..........
  consePGIintUNTBrapaA ..........  ..........  ..........  ..........  ..........
   ConsePGIintUNTRRH1  ..........  ..........  ..........  ..........  ..........
     PGIBo-EM:AF258277 TTGCTTAGCG  TCCAAATTTC  ATGATTGTAT  TCATTTGATT  GTTGTG....
     PGIBra-EM:AF258278 TTGCTTAGCG TCCAAATTTC  ATGATTGTAT  TCATTTGATT  GTTGTGTGAC
  consePGIintUNTBolera ..........  ..........  ..........  ..........  ..........
  consePGIintUNTR2000  ..........  ..........  ....TTG...  TCATT.GA..  .TTGT.TGCG
             Consensus                                                       1

101       --->                                     150
consePGIinTUNTDrakka   ..........  ......GTCG  TTTGTTGGTG  AGT.GAACAG  CAGTCATTTA
      consensWesrPGI   ..........  .GCCTGTTTG  TGTTATGATG  AAT.GAACAG  CAGTCATTTA
   consePGIintUNTR113  ..........  .GCCCGGTTG  .........G  TAT.GAAACG  CAG.CATTTA
  consePGIintUNTBrapaA ..........  ..........  ..........  ..........G CAGTCATTTA
   ConsePGIintUNTRRH1  ..........  ..........  ..........  ......CG  TGTTGAGAAG  CAG.CATTTA
     PGIBo-EM:AF258277 ......CCTG  TCGCCTTGTTG TGTTA.GATG  AAT.GAACAG  CAGTCATTTA
     PGIBra-EM:AF258278 TATCGCCTC. TCGCCTTGTTG TGTTATGATG  AAT.GAACAG  CAGTCATTTA
  consePGIintUNTBolera ..........  ..........  ..........  ..........  ..........
  consePGIintUNTR2000  ......CCTG  TCGCCTTGTTG TGTTATGATG  AAT.GAACA.  CAGTCATTTA
             Consensus ......[...]  ........t.g ......_...g ...t.gaa.ag cagtcattta 151            * MseI restriction site            200
consePGIinTUNTDrakka   ACATG.TGGT  TAACTTAACA  GGGCTCCGGC  TGTTGCAAAA  CACATGGTTG
      consensWesrPGI   ACATG.TGGT  TAACTTAACA  GGGCTCCGGC  TGTTGCAAAA  CACATGGTTG
   consePGIintUNTR113  ACATG.TGGT  .AACTGAACA  GGGCTCCGGC  TGTTGCCC..  CTAAGGGTTG
  consePGIintUNTBrapaA ACATGGTGGT  TAACTGAACA  GGGCTCCGGC  TGTTGCAAAA  CACATGGTTG
   ConsePGIintUNTRRH1  ACATG..GGT  ..ACTGAACA  GGGC.CCGGC  TGTTGCAA..  .ACAG...TG
     PGIBo-EM:AF258277 ACATG.TGGT  TAACTTAACA  GGGCTCAGGC  TGTTGCAAAA  CACATGGTTG
     PGIBra-EM:AF258278 ACATG.TGGT TAACTTAACA  GGGCTCCGGC  TGTTGCAAAA  CATATGGTTG
  consePGIintUNTBolera ..........  ..........  .........C  TGTTGCAAAA  CACATGGTTG
  consePGIintUNTR2000  ACATG.TGGT  TAACTTAACA  GGGCTCCGGC  TGTTGCAAAA  CACATGGTTG
             Consensus acatg.tggt  taact[.]aaca gggctccggc  tgttgcaaaa  cacatggttg
                                         2          []                   []

201  PGI int U --->                               250
consePGIinTUNTDrakka   CTGT  CAGCAC TAATCTTGC  GGTATG  AATT TGTGATTAAA  TTTGTTTGTT
      consensWesrPGI   CTGT  CAGCAC TAATCTTGC  GGTATG  AATT TGTGATTAAA  TTTGTTTGTT
   consePGIintUNTR113  CTGT  CAGCAC TAATCTTGC  GGTATG  AATT TGTGATTAAA  TTTGTTTGTT
  consePGIintUNTBrapaA CTGT  CAGCAC TAATCTTGC  GGTATG  AATT TGTGATTAAA  TTTGTTTGTT
   ConsePGIintUNTRRH1  CTGT  CAGCAC TAATCTTGC  GGTATG  AATT TGTGATTAAA  TTTGTTTGTT
     PGIBo-EM:AF258277 CTGT  CAGCAC TAATCTTGC  GGTATG  AATT TGTGATTAAA  TTTGTTTGTT
     PGIBra-EM:AF258278 CTGT CAGCAC TAATCTTGC  GGTATG  AATT TGTGATTAAA  TTTGTTTGTT
  consePGIintUNTBolera CTGT  CAGCAC TAATCTTGC  GGTATG  AATT TGTGATTAAA  TTTGTTTGTT
  consePGIintUNTR2000  CTGT  CAGCAC TAATCTTGC  GGTATG  AATT TGTGATTAAA  TTTGTTTGTT
             Consensus ctgtcagcac  taatcttgc   ggtatg  aatt tgtgattaaa  tttgtttgt 251                                               300
consePGIinTUNTDrakka   TGTGACTCTT  T.CTTCATTG  TTCGTTTTCG  TACAATAAAC  CGAATGTATA
      consensWesrPGI   TGTGACTCTT  T.CTTCATTG  TTCGTTTTCG  TACAATAAAC  CGAATGTATA
   consePGIintUNTR113  TGCGACTCTT  T.CTTCATTG  TTCGTTTTCG  TACAATAAAC  ..AATGTATA
  consePGIintUNTBrapaA TGCGACTCTT  T.CTTCATTG  TTCGTTTTCG  TACAATAAAC  ..AATGTATA
   ConsePGIintUNTRRH1  TGCGACTCTT  T.CTTCATTG  TTCGTTTTCG  TACAATAAAC  ..AATGTATA
     PGIBo-EM:AF258277 TGTGACTCTT  T.CTTCATTG  TTCGTTTTCG  TACAATAAAC  CGAATGTATA
     PGIBra-EM:AF258278 TGTGACTCTT TTCTTCATTG  TTCGTTTTCG  TACAATAAAC  CGAATGTATA
  consePGIintUNTBolera TG.GACTCTT  T.CTTCATTG  TTCGTTTTCG  TACAATAAAC  CGAATGTATA
  consePGIintUNTR2000  TGTGACTCTT  T.CTTCATTG  TTCGTTTTCG  TACAATAAAC  CGAATGTATA
             Consensus tg.gactctt  t_cttcattg  ttcgttttcg  tacaataaac  cgaatgtata
                                        []                                  []3
```

Figure 13 (b)

```
                    301                    <---    PGIo1_antL 341         350
consePGIinTUNTDrakka   ATCTTTTTAC AAACTGAA  TT TTCTACCGGG TCTGATGTAC A  ATGCTAGTC
     consensWesrPGI    ATCTTTTTAC AAACTGAA  TT TTCTACCGGG TCTGATGTAC A  ATGCTAGTC
  consePGIintUNTR113   ATCTTTTTAC AAACTGAA  TT TTCTACCGGG TCTGATGTAC A  ATGCTAGTC
 consePGIintUNTBrapaA  ATCTTTTTAC AAACTGAA  TT TTCTACCGGG TCTGATGTAC A  ATGCTAGTC
  ConsePGIintUNTRRH1   ATCTTTTTAC AAACTGAA  TT TTCTACCGGG TCTGATGTAC A  ATGCTAGTC
    PGIBo-EM:AF258277  ATCTTTTTAC AAACTGAA  TT TTCTACCGGG TCTGATGTAC A  ATGCTAGTC
    PGIBra-EM:AF258278 ACCTTTTTAC AAACTGAA  AT GTCTACCGGG TCTGATGTAC A  ATGCTAGTC
 consePGIintUNTBolera  ATCTTTTTAC AAACTGAA  TT TTCTACCGGG TCTGATGTAC A  ATGCTAGTC
 consePGIintUNTR2000   ATCTTTT.AC AAACTGAA  TT TTCTACCGGG TCTGATGTAC A  ATGCTAGTC
          Consensus    atcttttac  aaactgaa  tt ttctaccggg tctgatgtac a  atgctAGTC
```

Figure 14 (a)

```
                      201  PGI int U --->                                                      250
consePGIinTUNTDrakka   CTGT CAGCAC TAATCTTGC GGTATG AATT TGTGATTAAA TTTGTTTGTT
    consensWesrPGI     CTGT CAGCAC TAATCTTGC GGTATG AATT TGTGATTAAA TTTGTTTGTT
   consePGIintUNTR113  CTGT CAGCAC TAATCTTGC GGTATG AATT TGTGATTAAA TTTGTTTGTT
   consePGIintUNTBrapaA CTGT CAGCAC TAATCTTGC GGTATG AATT TGTGATTAAA TTTGTTTGTT
   ConsePGIintUNTRRH1  CTGT CAGCAC TAATCTTGC GGTATG AATT TGTGATTAAA TTTGTTTGTT
     PGIBo-EM:AF258277 CTGT CAGCAC TAATCTTGC GGTATG AATT TGTGATTAAA TTTGTTTGTT
     PGIBra-EM:AF258278 CTGT CAGCAC TAATCTTGC GGTATG AATT TGTGATTAAA TTTGTTTGTT
   consePGIintUNTBolera CTGT CAGCAC TAATCTTGC GGTATG AATT TGTGATTAAA TTTGTTTGTT
   consePGIintUNTR2000 CTGT CAGCAC TAATCTTGC GGTATG AATT TGTGATTAAA TTTGTTTGTT
            Consensus  ctgtcagcac taatcttgc ggtatg aatt tgtgattaaa tttgtttgt 251                                                                       300
consePGIinTUNTDrakka   TGTGACTCTT T.CTTCATTG TTCGTTTTCG TACAATAAAC CGAATGTATA
    consensWesrPGI     TGTGACTCTT T.CTTCATTG TTCGTTTTCG TACAATAAAC CGAATGTATA
   consePGIintUNTR113  TGCGACTCTT T.CTTCATTG TTCGTTTTCG TACAATAAAC ..AATGTATA
   consePGIintUNTBrapaA TGCGACTCTT T.CTTCATTG TTCGTTTTCG TACAATAAAC ..AATGTATA
   ConsePGIintUNTRRH1  TGCGACTCTT T.CTTCATTG TTCGTTTTCG TACAATAAAC ..AATGTATA
     PGIBo-EM:AF258277 TGTGACTCTT T.CTTCATTG TTCGTTTTCG TACAATAAAC CGAATGTATA
     PGIBra-EM:AF258278 TGTGACTCTT TTCTTCATTG TTCGTTTTCG TACAATAAAC CGAATGTATA
   consePGIintUNTBolera TG.GACTCTT T.CTTCATTG TTCGTTTTCG TACAATAAAC CGAATGTATA
   consePGIintUNTR2000 TGTGACTCTT T.CTTCATTG TTCGTTTTCG TACAATAAAC CGAATGTATA
            Consensus  tg.gactctt t.cttcattg ttcgttttcg tacaataaac cgaatgtata
                                             ε                              ε3

301                  <--- PGIol antL 341              350
consePGIinTUNTDrakka   ATCTTTTTAC AAACTGAA TT TTCTACCGGG TCTGATGTAC A ATGCTAGTC
    consensWesrPGI     ATCTTTTTAC AAACTGAA TT TTCTACCGGG TCTGATGTAC A ATGCTAGTC
   consePGIintUNTR113  ATCTTTTTAC AAACTGAA TT TTCTACCGGG TCTGATGTAC A ATGCTAGTC
   consePGIintUNTBrapaA ATCTTTTTAC AAACTGAA TT TTCTACCGGG TCTGATGTAC A ATGCTAGTC
   ConsePGIintUNTRRH1  ATCTTTTTAC AAACTGAA TT TTCTACCGGG TCTGATGTAC A ATGCTAGTC
     PGIBo-EM:AF258277 ATCTTTTTAC AAACTGAA TT TTCTACCGGG TCTGATGTAC A ATGCTAGTC
     PGIBra-EM:AF258278 ACCTTTTTAC AAACTGAA AT GTCTACCGGG TCTGATGTAC A ATGCTAGTC
   consePGIintUNTBolera ATCTTTTTAC AAACTGAA TT TTCTACCGGG TCTGATGTAC A ATGCTAGTC
   consePGIintUNTR2000 ATCTTTT.AC AAACTGAA TT TTCTACCGGG TCTGATGTAC A ATGCTAGTC
            Consensus  atcttttttac aaactgaa tt ttctaccggg tctgatgtac a atgctAGTC
                        ε

351                                                                       400
consePGIinTUNTDrakka   TCCATGTTCT TGGGGATCAT GATTTATTTT CTACATGTAT TCAGACAGTA
    consensWesrPGI     TCCATGTTCT TGGGGATCAT GATTTATTTT CT.CATGTAT TCAGACAGTA
   consePGIintUNTR113  TCCATGTTCT TGGGGATCAT GATTTATTTT CTACATGTGT TCAGCCAGTA
   consePGIintUNTBrapaA TCCATGTTCT TGGGGATCAT GATTTATTTT CTACATGTGT TCAGCCAGTA
   ConsePGIintUNTRRH1  TCCATGTTCT TGGGGATCAT GATTTATTTT CTACATGTGT TCAGCCAGTA
     PGIBo-EM:AF258277 TCCATGTTCT TGGGGATCAT GATTTATTTT CTACATGTAT TCAGACAGTA
     PGIBra-EM:AF258278 TCCATGTTCT TGGGGATCAT GATTTATTTT CTACATGTAT TCAGACAGTA
   consePGIintUNTBolera TCCATGTTCT TGGGGATCAT GATTTATTTT CTACATGTAT TCAGACAGTA
   consePGIintUNTR2000 TCCATGTTCT TGGGGATCAT GATTTATTTT CTACATGTAT TCAGACAGTA
            Consensus  TCCATGTTCT TGGGGATCAT GATTTATTTT CTaCATGTaT TCAGaCAGTA
                                                                    ε5        ε6

401                                                                       450
consePGIinTUNTDrakka   CAGAAGAAAG TGTTCAAAAC TCTGGATGTT TTAATTTACA GTTAGTGGAG
    consensWesrPGI     CAGAAGAAAG TGTTCAAAAC TCTGGATGTT TTAATTTACA GTTAGTGGAG
   consePGIintUNTR113  CAGAAGAAAG TGTTTAAAAC TCTGGATGTT TTAATTTACA GTTAGTGGAG
   consePGIintUNTBrapaA CAGAAGAAAG TGTTTAAAAC TCTGGATGTT TTAATTTACA GTTAGTGGAG
   ConsePGIintUNTRRH1  CAGAAGAAAG TGTTTAAAAC TCTGGATGTT TTAATTTACA GTTAGTGGAG
     PGIBo-EM:AF258277 CAGAAGAAAG TATTTAAAAC TCTGGATGTT TTAATTTACA GTTAGTGGAG
     PGIBra-EM:AF258278 CAGAAGAAAA TGTTTAAAAC TCTGGATGTT TTGATTTACA GTTAGTGGAG
   consePGIintUNTBolera CAGAAGAAAG TGTTCAAAAC TCTGGATGTT TTAATTTACA GTTAGTGGAG
   consePGIintUNTR2000 CAGAAGAAAG TGTTCAAAAC TCTGGATGTT TTAATTTACA GTTAGTGGAG
            Consensus  CAGAAGAAAg TgTTcAAAAC TCTGGATGTT TTaATTTACA GTTAGTGGAG
                              ε7                              ε
```

Figure 14 (b)

```
                         451        end of Data Base PGI sequences        500
consePGIinTUNTDrakka     AAGTTCGGCA TTGATCCGAA CAATGCATTT GCATTTTGGG ACTGGGTTGG
       consensWesrPGI    AAGTTCGGCA TTGATCCGAA CAATGCATTT GCATTTTGGG ACTGGGTTGG
     consePGIintUNTR113  AAGTTCGGCA TTGATCCGAA CAATGCATTT GCATTTTGGG ACTGGGTTGG
   consePGIintUNTBrapaA  AAGTTCGGCA TTGATCCGAA CAATGCATTT GCATTTTGGG ACTGGGTTGG
     ConsePGIintUNTRRH1  AAGTTCGGCA TTGATCCGAA CAATGCATTT GCATTTTGGG ACTGGGTTGG
       PGIBo-EM:AF258277 AAGTTCGGCA TTGATCC... .......... .......... ..........
       PGIBra-EM:AF258278 AAGTTCGGCA TTGATCCGAA CAA....... .......... ..........
     consePGIintUNTBolera AAGTTCGGCA TTGATCCGAA CAATGCATTT GCATTTTGGG ACTGGGTTGG
     consePGIintUNTR2000  AAGTTCGGCA TTGATCCGAA CAATGCATTT GCATTTTGGG ACTGGGTTGG
               Consensus  AAGTTCGGCA TTGATCCgaa caatgcattt gcattttggg actgggttgg 501                                              550
consePGIinTUNTDrakka     TGGAAGGTAC AGTGGTAAGT GCTTGTTTAT TTGGTTGTAT AAATTTCTCG
       consensWesrPGI    TGGAAGGTAC AGTGGTAAGT GCTTGTTTAT TTGGTTGTAT AAATTTCTCG
     consePGIintUNTR113  TGGAAGGTAC AGTGGTAAGT GCTTGTTTAT TTGGTTGTAT TAATTTCTCA
   consePGIintUNTBrapaA  TGGAAGGTAC AGTGGTAAGT GCTTGTTTAT TTGGTTGTAT TAATTTCTCA
     ConsePGIintUNTRRH1  TGGAAGGTAC AGTGGTAAGT GCTTGTTTAT TTGGTTGTAT TAATTTCTCA
       PGIBo-EM:AF258277 .......... .......... .......... .......... ..........
       PGIBra-EM:AF258278 .......... .......... .......... .......... ..........
     consePGIintUNTBolera TGGAAGGTAC AGTGGTAAGT GCTTGTTTAT TTGGTTGTAT AAATTTCTCG
     consePGIintUNTR2000  TGGAAGGTAC AGTGGTAAGT GCTTGTTTAT TTGGTTGTAT AAATTTCTCG
               Consensus  tggaaggtac agtggtaagt gcttgtttat ttggttgtat [.]aatttctc[.]
                                                                     8          9

551                                              600
consePGIinTUNTDrakka     TCCATTTCCG CTTGCTTAGT GTATAACTGA AATTCTTTTG CAGTTTGCAG
       consensWesrPGI    TCCATTTCCG CTTGCTTAGT GTATAACTGA AATTCTTTTG CAGTTTGCAG
     consePGIintUNTR113  TCCATATCCG CTTGCTTAGT TTATAACTGA AATTCTTTTG CAGTTTGCAG
   consePGIintUNTBrapaA  TCCATATCCG CTTGCTTAGT TTATAACTGA AATTCTTTTG CAGTTTGCAG
     ConsePGIintUNTRRH1  TCCATATCCG CTTGCTTAGT TTATAACTGA AATTCTTTTG CAGTTTGCAG
       PGIBo-EM:AF258277 .......... .......... .......... .......... ..........
       PGIBra-EM:AF258278 .......... .......... .......... .......... ..........
     consePGIintUNTBolera TCCATTTCCG CTTGCTTAGT GTATAACTGA AATTCTTTTG CAGTTTGCAG
     consePGIintUNTR2000  TCCATTTCCG CTTGCTTAGT GTATAACTGA AATTCTTTTG CAGTTTGCAG
               Consensus  tccat[.]tccg cttgcttagt [.]tataactga aattcttttg cagtttgcag
                              10                11

601                                              650
consePGIinTUNTDrakka     TGCTGTTGGA GTCTTACCAT TGTCTCTACA GTATGGCTTC TCTGTGGTTG
       consensWesrPGI    TGCTGTTGGA GTCTTACCAT TGTCTCTACA GTATGGCTTC TCTGTGGTTG
     consePGIintUNTR113  TGCTGTTGGA GTCTTACCAT TGTCTCTACA GTATGGCTTC TCCGTGGTTG
   consePGIintUNTBrapaA  TGCTGTTGGA GTCTTACCAT TGTCTCTACA GTATGGCTTC TCCGTGGTTG
     ConsePGIintUNTRRH1  TGCTGTTGGA GTCTTACCAT TGTCTCTACA GTATGGCTTC TCCGTGGTTG
       PGIBo-EM:AF258277 .......... .......... .......... .......... ..........
       PGIBra-EM:AF258278 .......... .......... .......... .......... ..........
     consePGIintUNTBolera TGCTGTTGGA GTCTTACCAT TGTCTCTACA GTATGGCTTC TCTGTGGTTG
     consePGIintUNTR2000  TGCTGTTGGA GTCTTACCAT TGTCTCTACA GTATGGCTTC TCTGTGGTTG
               Consensus  tgctgttgga gtcttaccat tgtctctaca gtatggcttc tc[.]gtggttg
                                                                        12

651                                              700
consePGIinTUNTDrakka     AGAAGTACGG TACCTTCTAC TTTATCAGCC ATCTCATAAA ATGTCTTAGG
       consensWesrPGI    AGAAGTACGG TACCTTCTAC TTTATCAGCC ATCTCATAAA ATGTCTTAGG
     consePGIintUNTR113  AGAAGTACGG TACCTTCTAC TTTATTAGCC ATCTCATAAA ATGTCTTGGG
   consePGIintUNTBrapaA  AGAAGTACGG TACCTTCTAC TTTATTAGCC ATCTCATAAA ATGTCTTGGG
     ConsePGIintUNTRRH1  AGAAGTACGG TACCTTCTAC TTTATTAGCC ATCTCATAAA ATGTCTTGGG
       PGIBo-EM:AF258277 .......... .......... .......... .......... ..........
       PGIBra-EM:AF258278 .......... .......... .......... .......... ..........
     consePGIintUNTBolera AGAAGTACGG TACCTTCTAC TTTATCAGCC ATCTCATAAA A.GTCTTAGG
     consePGIintUNTR2000  AGAAGTACGG TACCTTCTAC TTTATCAGCC ATCTCATAAA ATGTCTTAGG
               Consensus  agaagtacgg taccttctac tttat[.]agcc atctcataaa atgtctt[.]gg
                                                      13                    14
```

Figure 14 (c)

```
                         701                                                            750
consePGIinTUNTDrakka     CATATTCTTT CTATTTTATT TTCCTCTTAA TGATTTCTTC TTTTTTTTAT
      consensWesrPGI     CATATTCTTT CTATTTTATT TTCCTCTTAA TGATTTCTTC TTTTTTTTAT
   consePGIintUNTR113    CATATTCTTT CTATTTTATT TTCCTCTGAA TGATTTCTTC TCTTTTAT..
  consePGIintUNTBrapaA   CATATTCTTT CTATTTTATT TTCCTCTGAA TGATTTCTTC TCTTTTAT..
   ConsePGIintUNTRRH1    CATATTCTTT CTATTTTATT TTCCTCTGAA TGATTTCTTC TCTTTTAT..
     PGIBo-EM:AF258277   .......... .......... .......... .......... ..........
     PGIBra-EM:AF258278  .......... .......... .......... .......... ..........
   consePGIintUNTBolera  CATATTCTTT CTATTTTATT TTCCTCTTAA TGATTTCTTC TTTTTTTA..
   consePGIintUNTR2000   CATATTCTTT CTATTTTATT TCCCTCTTAA TGATTTCTTC TTTTTTTTAT
             Consensus   catattcttt ctattttatt ttcctct.aa tgatttcttc t.tttt.t..
                                                    15                  16   17
                         751                                                            800
consePGIinTUNTDrakka     TGCATTCCCG TTTTATTTTC AAAAGTTGTT ACTGTCTCTA AATCAAGAAG
      consensWesrPGI     TGCATTCCCG TTTTATTTTC AAAAGTTGTT ACTGTCTCTA AATCAAGAAG
   consePGIintUNTR113    TGCATTCCCG TTTTATTTTC AAAAGTTGTC ACTGTCTCTA AATCAAGAAG
  consePGIintUNTBrapaA   TGCATTCCCG TTTTATTTTC AAAAGTTGTC ACTGTCTCTA AATCAAGAAG
   ConsePGIintUNTRRH1    TGCATTCCCG TTTTATTTTC AAAAGTTGTC ACTGTCTCTA AATCAAGAAG
     PGIBo-EM:AF258277   .......... .......... .......... .......... ..........
     PGIBra-EM:AF258278  .......... .......... .......... .......... ..........
   consePGIintUNTBolera  TGCATTCCCG TTTTATTT.C AAAAGTTGTC CGGCCCCCTA AACCAAGAAG
   consePGIintUNTR2000   TGCATTCCCG TTTTATTTTC AAAAGTTGTT ACTGTCTCTA AATCAAGAAG
             Consensus   tgcattcccg ttttatttc aaaagttgt. actgtctcta aatcaagaag 801                                                            850
consePGIinTUNTDrakka     AAACCTTCTT AGTAGATCCA GCTGATATTC AGCCTTTTTT AAATTGGACT
      consensWesrPGI     AAACCTTCTT AGTAGATCCA GCTGATATTC AGCCTTTTTT AAATTGGACT
   consePGIintUNTR113    AAACCTTCTT AGTAGATCCA GTTGATATTC AGCCTTTTCT AAATTGGACT
  consePGIintUNTBrapaA   AAACCTTCTT AGTAGATCCA G.TGATATTC AGCCTTTTCT AAATTGGACT
   ConsePGIintUNTRRH1    AAACCTTCTT AGTAGATCCA GTTGATATTC AGCCTTTTCT AAATTGGACT
     PGIBo-EM:AF258277   .......... .......... .......... .......... ..........
     PGIBra-EM:AF258278  .......... .......... .......... .......... ..........
   consePGIintUNTBolera  AAACCTTTCT AGGA...CCA GA....CTCC ACCCTTTTTT AAATTGGACT
   consePGIintUNTR2000   AAACCTTCTT AGTAGATCCA GCTGATATTC AGCCTTTTTT AAATTGGACT
             Consensus   aaaccttctt agtagatcca g..tgatattc agcctttt.t aaattggact
                                                    18                  19

851                                                            900
consePGIinTUNTDrakka     GCAGGTTTTT AAA.GGGAGC TTCAAGCATT GATAAGCATT TCCAGTCCCC
      consensWesrPGI     GCAGGTTTTT AAA.GGGAGC TTCAAGCATT GATAAGCATT TCCAGTCCAC
   consePGIintUNTR113    GCAGGTTTTT AAA.GGGAGC TTCAAGCATT GATCAGCATT TCCAGTCC..
  consePGIintUNTBrapaA   GCAGGTTTTT AAA.GGGAGC TTCAAGCATT GATCAGCATT TCCAGTCC..
   ConsePGIintUNTRRH1    GCAGGTTTTT AAA.GGGAGC TTCAAGCATT GATCAGCATT TCCAGTCCAC
     PGIBo-EM:AF258277   .......... .......... .......... .......... ..........
     PGIBra-EM:AF258278  .......... .......... .......... .......... ..........
   consePGIintUNTBolera  GCAGGTTTTT AAA.GGGGGC TTCAAGCATT GATAAGCATT TCCAGTCCAC
   consePGIintUNTR2000   GCAGGTTTTT AAACGGGAGC TTCAAGCATT GATAAGCATT TCCAGTCCAC
             Consensus   gcaggttttt aaa.gggagc ttcaagcatt gat.agcatt tccagtcc.c
                                                                20

901                                                            950
consePGIinTUNTDrakka     ACC.GTTTGA GAAGAATATA CCCGTGAGTT GCATTAGTTT GTGTGATTAT
      consensWesrPGI     ACC.GTTTGA GAAGAATATA CCCGTGAGTT GCATTAGTT. GTGTGATTAT
   consePGIintUNTR113    .CCCGTTTGA GAAGAATATA CCCGTGAGTT GCATTAGTT. ...GTGATTAT
  consePGIintUNTBrapaA   .CCCGTTTGA GAAGAATATA CCCGTGAGTT GCATTAGTT. GTGTGATTAT
   ConsePGIintUNTRRH1    ACC.GTTTGA GAAGAATATA CCCGTGAGTT GCATTAGTT. GTGTGATTAT
     PGIBo-EM:AF258277   .......... .......... .......... .......... ..........
     PGIBra-EM:AF258278  .......... .......... .......... .......... ..........
   consePGIintUNTBolera  ACCCGTTTGA GAAGAATATA CCCGTGAGTT GCATTAGTT. GTGTGATTAT
   consePGIintUNTR2000   ACC.GTTTGA GAAGAATATA CCCGTGAGTT GCATTAGTT. GTGTGATTAT
             Consensus   acc.gtttga gaagaatata cccgtgagtt gcattagtt. gtgtgattat
```

Figure 14 (d)

```
                        951                                                      1000
consePGIinTUNTDrakka    ACAGTTTTTC TTGTCTTTTT GCTATGCCCA TCAACACTAG AAGATTCGTG
      consensWesrPGI    ACAGTTTT.C TTGTCTTTT. GCTATGTCCA TCAACACTAG A.GATTCGTG
    consePGIintUNTR113  ACAGTTTT.C TTGCCTTTTT GCTAT..AGG GCAAC.CTAG A.GATTCATG
   consePGIintUNTBrapaA ACAGTTTT.C TTGTCTTTT. GCTATG.TCA TCAAC.CTAG A.GATTCATG
   ConsePGIintUNTRRH1   ACAGTTTT.C TTGTCTTTTT GCTAT...AT GCAACCCTAG ..GATTCATG
      PGIBo-EM:AF258277 .......... .......... .......... .......... ..........
      PGIBra-EM:AF258278 .......... .......... .......... .......... ..........
   consePGIintUNTBolera ACAGTTTT.C TTGTCTTTTT GCTAG..TGA TCAAC.CTAG A.GATTCGTG
   consePGIintUNTR2000  ACAGTTTT.C TTGTCTTTTT GCTATGTCCA TCAACACTAG A.GATTCGTG
            Consensus   acagtttt.c ttgtctttt. gctat....a tcaac.ctag a.gattc.tg
                                                                            21

1001                                                     1050
consePGIinTUNTDrakka    AAGTTATTAG TGTAGCCAAC GCCTAGGGGG AGGTTGGTTG GCTGTTTTGG
      consensWesrPGI    AAGTTATTAG TGTAGTCAAC GCA....... .......... ..........
    consePGIintUNTR113  AAGTTATTAG TGTAGTCAAC GCAGAGGAGA G..TTCACTG ACGG......
   consePGIintUNTBrapaA AAGTTATTAG TGTAGTCAAC GCAGAGTGAG AGG.TGATTG ..........
   ConsePGIintUNTRRH1   AAGTTATTAG TGTAGTCAAC GCAGAGGAGG AGATGGTT.. ..........
      PGIBo-EM:AF258277 .......... .......... .......... .......... ..........
      PGIBra-EM:AF258278 .......... .......... .......... .......... ..........
   consePGIintUNTBolera AAGTTATTAG TGTAGTCAAC GCATAGGAGG AGC....... ..........
   consePGIintUNTR2000  AAGTTATTAG TGTAGTCAAC GCATAGGGAG AGGTGAT.GG TGACTTTTGG
            Consensus   aagttattag tgtagtcaac gca.agg.g. .g........ ..........

1051            1076
consePGIinTUNTDrakka    ACGTTTTCAC GTGCTCCGGG GGGTTTTTGG GGACCAAACC CCCAAC
      consensWesrPGI    .......... .......... .......... .......... ......
    consePGIintUNTR113  .......... .......... .......... .......... ......
   consePGIintUNTBrapaA .......... .......... .......... .......... ......
   ConsePGIintUNTRRH1   .......... .......... .......... .......... ......
      PGIBo-EM:AF258277 .......... .......... .......... .......... ......
      PGIBra-EM:AF258278 .......... .......... ,......... .......... ......
   consePGIintUNTBolera .......... .......... .......... .......... ......
   consePGIintUNTR2000  ACGATTTCAG GTGCTTTAGG GTTATTG... .......... ......
```

Figure 15 (a)

```
                        51                                                      100
         EMBH44836anti  .......... .......... .......... .......... ..........
       GCP18-5CP418L-Sams .......... .......... .......... .......... ..........
       GCP18-2CP418L-Wes  .......... .......... .......... .......... ..........
     GCP18-4CP418L-R2000  .......... .......... .......... .......... [CP418L]...
        conse129ba1-Drak  .......... .......... AAACAAATCA AAATTCTAAA TTTCTCCA
       GCPS18-129Sam-ba2  ...... . AAAC TATGTA ACAAAAATCA AAATTGTAAA TGTCTCCA
       GCPR18-3129R211-ba2 ..... ..... AA CCAAAAATCC AAATTGTAAA TGTTCCCT.
       GCP18-10129R20-ba2  .......... .......... CAAAATCCA AAATTGTAAA TGTC.CCT
              Consensus   .......... .......... .......... .......... ..........

101                                                     150
         EMBH44836anti   .......... .......... .......... .......... ..........
       GCP18-5CP418L-Sams .......... .......... ........AT A.CATTTTCT GTAA
       GCP18-2CP418L-Wes  .......... .......... .AGG  T.AT A.CATTTTCT GTAA
     GCP18-4CP418L-R2000  .......... .......... .AGG  TCAT A.CATTTTCT GTAA
        conse129ba1-Drak  TCACAAGGAC CTACAGAATA GAGTTATCAT AACATTT CT GTAA
       GCPS18-129Sam-ba2  TCGTAACGAC .TACAGAATA GAGTTATCAT AACATTTTCT G AA
       GCPR18-3129R211-ba2 TGGTAACGGC CTCAAAAA.A GAGGTATCAA AAC.TTTTCT GT.A
       GCP18-10129R20-ba2. TGGTTACCGC C.CAAAAA.A AAGGT..CAA AACTT.TCCG GTAA
              Consensus   .......... .......... .......... .......... ..........

151                                                     200
         EMBH44836anti   .......... .......... .......... .......... ..........
       GCP18-5CP418L-Sams .TATTTCCAT CAAAATGA... .CTAGAGAAC AGCAGTTCTT ATAACATTAT
       GCP18-2CP418L-Wes  .TATTTCCAT CAAAATGA... .CTAGAGAAC AG.AGTTCTT ATAACATTAT
     GCP18-4CP418L-R2000  ATATTTCCAT CAAAATGA... .CTAGAGAAC AG.AGTTCTT ATAACATTAT
        conse129ba1-Drak  ATATTTCCAT CAAAATGA... .CTAGAGAAC AG.AGTTCTT ATAACATTAT
       GCPS18-129Sam-ba2  ATGTTTCCAT CAAAATGA    CTATCGGAC ATAATTAAT ATA.CATTTT
       GCPR18-3129R211-ba2 ATGTTTCCAT CAAAATG.    CTATCGGAC ATAATTAAT ATAAC.TTCT
       GCP18-10129R20-ba2 ATGTTTCCAT CAAAATG.    CTTCGGA.C ATAATTAAT ATAAC.TTCT
              Consensus   ATGTTTCCCT CAAA.TGG    CTTCGGA.C ATAATTAAA A...CATTCT 201                                                     250
         EMBH44836anti   .......... .......... .......... .......... ..........
       GCP18-5CP418L-Sams CTGTAAA TG.TTCCAA CAAAA CCACT ACATAGCAGAGTTC .TTATAACAT
       GCP18-2CP418L-Wes  CTGTAAA TG.TTCCAA CAAAA CCACT ACATAGCAGAGTTC ATTATAACAT
     GCP18-4CP418L-R2000  CTGTAAA TG.TTCCAA CAAAA CCACT ACATAGCAGAGTTC .TTATAACAT
        conse129ba1-Drak  CTGTAAA TG.TTCCAA CAAAA CCACT ACATAGCAGAGTTC .TTATAACAT
       GCPS18-129Sam-ba2  CTG.AAAAT AATTCC CCTCAAAAATTA.] .CATT    TTC TTACAA.A.]
       GCPR18-3129R211-ba2 CTG.AAAAT.ATTCC CT CAAAA TTA.] ACATT     TTC T.ACAA.A.]
       GCP18-10129R20-ba2 CTG.AAA.TAATTCC CT CAAAA TTA.] ACAT.      TTC T.ACAA.A.]
              Consensus   ---------- ---------- ---------- ---------- ----------

251                                                     300
         EMBH44836anti   .......... .......... .......... .......... ...CTATACC
       GCP18-5CP418L-Sams TGTCTGT.AA ATGTCCAATC AAAACCACTA CAGAACAAAG CTCCTATAAC
       GCP18-2CP418L-Wes  TGTCTGT.AA ATGTCCAATC AAAACCACTA CAGAACAAAG CTCCTATAAC
     GCP18-4CP418L-R2000  TGTCTGT.AA ATGTCCAATC AAAACCACTA CAGAACAAAG CTCCTATAAC
        conse129ba1-Drak  TGTCTGT.AA ATGTCCAATC AAAACCACTA CAGAACAAAG CTCCTATAAC
       GCPS18-129Sam-ba2  TGTTTC... .......... .......... CATCAAAATG AGACTCCA.G
       GCPR18-3129R211-ba2 TGTTTC... .......... .......... CATCAAAATG AGACTACA.G
       GCP18-10129R20-ba2 TGTTTC... .......... .......... CATCAAAATG AGACTACA.G
              Consensus   tttctgt.aa tgtttccatc aaaatgacta tcgaacataa ttaatAtaac 301                                                     350
         EMBH44836anti   A  TTGTTT ATACAAAGTT TCACT AAAT CTACAAACTT CCCCCGTAAA
       GCP18-5CP418L-Sams A  TTGTTT ATACAAGTTT .CACT AAAT CTACAAACTT TCCCCGTAAA
       GCP18-2CP418L-Wes  A  TTGTTT ATACAAAGTT TCACT AAAT CTACAAACTT TCCCCGTAAA
     GCP18-4CP418L-R2000  A  TTGTTT ATACAAGTTT .CACT AAAT CTACAAACTT TCCCCGTAAA
        conse129ba1-Drak  A.  TGTTT ATACAAAGTT TCACT AAAT CTACAAACTT TCCCCGTAAA
       GCPS18-129Sam-ba2  AAC.CAGTTC TTGCATAGTT TCACTTAAAT CTACAAACTT TC........
       GCPR18-3129R211-ba2 AACACAGTTC TTGCATAGTT TCACT.AAAT CTACAAACTT TC........
       GCP18-10129R20-ba2 A.CCCAGTTC TTGCATAGTT TC.CT.AAAT CTTCAAACTT TC........
              Consensus   ---------- ---------- ---------- ---------- ----------
```

Figure 15 (b)

```
                          351                                                              400
         EMBH44836anti    TGAGCTTAAT ATCACCCAA. GATGTTTCA ATCAGAT AAA GAGTAACGAC
      GCP18-5CP418L-Sams  TGAGCTTAAT ATCACCCAAA GATGTTTCA ATCAGAT AAA GAGTAACGAC
       GCP18-2CP418L-Wes  TGAGCTTAAT ATCACCCAAA GATGTTTCA ATCAGAT AAA GAGTAACGAC
     GCP18-4CP418L-R2000  TGAGCTTAAT ATCACCCAAA GATGTTTCA ATCAGAT AAA GAGTAACGAC
         conse129ba1-Drak TGAGCTTAAT ATCACCCAAA GATGTTTCA ATCAGAT AAA GAGTA.CGAC
       GCPS18-129Sam-ba2  [.......]AAT CTTATCTAAA G.TTATCAC ATCACAT GAA GA[......]
      GCPR18-3129R211-ba2 [.......]AAT CTTATCTAA. G.TTATCAC ATCACAT GAA GA[......]
       GCP18-10129R20-ba2 [.......]AAT CTTATCTAAA G.TTATCAC ATCACAT GAA GA[......]
              Consensus   ---------- ---------- ---------- ---------- --- ----------

401
         EMBH44836anti    ATCGTTTTGA GATTAGAACA AA
      GCP18-5CP418L-Sams  ATCGTTTTGA GATTAGAACA AA
       GCP18-2CP418L-Wes  ATCGTTTTGA GATTAGAACA AA
     GCP18-4CP418L-R2000  ATCGTTTTGA GATTAGAACA AA
         conse129ba1-Drak ATCGTTTTGA GATTAGAACA AA
       GCPS18-129Sam-ba2  [.... ..........]GAGC AA
      GCPR18-3129R211-ba2 [.... ............]GGC AA
       GCP18-10129R20-ba2 [.... ............]GGC A.
              Consensus 431                                                              480
         EMBH44836anti    CTGAAACTTA CGTAGAGTGA TTTGAGGAGT AGGCTCGTTG CCAGCAGAGC
      GCP18-5CP418L-Sams  CTGAAACTTA CGTAGAGTGA TTTGAGGAGT AGGCTCGTTG CCAGCAGAGC
       GCP18-2CP418L-Wes  CTGAAACTTA CGTAGAGTGA TTTGAGGAGT AGGCTCGTTG CCAGCAGAG.
     GCP18-4CP418L-R2000  CTGAAACTTA CGTAGAGTGA TTTGAGGAGT AGGCTCGTTG CCAGCAGAGC
         conse129ba1-Drak CTGAAACTTA CGTAGAGTGA TTTGAGGAGT AGGCTCGTTG CCAGCAGAGC
       GCPS18-129Sam-ba2  GTAAACCTTA CCTAGAGTGA TCTGAGGAGT AGGCTCGTTG CCAGCGGAGC
      GCPR18-3129R211-ba2 GTAAACCTTA CCTAGAGTGA TCTGAGGAGT AGGCTCGTTG CCAGCGGAGC
       GCP18-10129R20-ba2 GTAA.CCTTA CCTAGAGTGA TCTGAGGAGT AGGCTCGTTG CCAGCGGAGC
              Consensus   .t.aa.ctta c.tagagtga t.tgaggagt aggctcgttg ccagc.gagc 481                                                              530
         EMBH44836anti    TAGCTCTCTC CTCCGCCTCA TGAAGCATCT GTTGCACCTG AGACAACCGT
      GCP18-5CP418L-Sams  TAGCTCTCTC CTCCGCCTCA TGAAGCATCT GTTGCACCTG AGACAACCGT
       GCP18-2CP418L-Wes  TAGCTCTCTC CTCCGCCTCA TGAAGCATCT GTTGCACCTG AGACAACCGT
     GCP18-4CP418L-R2000  TAGCTCTCTC CTCCGCCTCA TGAAGCATCT GTTGCACCTG AGACAACCGT
         conse129ba1-Drak TAGCTCTCTC CTCCGCCTCA TGAAGCATCT GTTGCACCTG AGACAACCGT
       GCPS18-129Sam-ba2  TAGCTCTCTC CTCC.CCTCA TGAAGCATCT GCTGCACCTG AGACAACCGT
      GCPR18-3129R211-ba2 TAGCTCTCTC CTCCGCCTCA TGAAGCATCT GCTGCACCTG AGACAACCGT
       GCP18-10129R20-ba2 TAGCTCTCTC CTCCGCCTCA TGAAGCATCT GCTGCACCTG AGACA.CCGT
              Consensus   tagctctctc ctccgcctca tgaagcatct g.tgcacctg agacaaccgt 531                                                              580
         EMBH44836anti    GACGAAACTT TCCGATCACC GCCACCAGAA TTCGACGCCG CGCATCGGAA
      GCP18-5CP418L-Sams  GACGAAACTT TCCGATCACC GCCACCAGAA TTCGACGCCG CGCATCGGAA
       GCP18-2CP418L-Wes  GACGAAACTT TCCGATCACC GCCACCAGAA TTCGACGCCG CGCATCGGAA
     GCP18-4CP418L-R2000  GACGAAACTT TCCGATCACC GCCACCAGAA TTCGACGCCG CGCATCGGAA
         conse129ba1-Drak GACGAAACTT TCCGATCACC GCC.CCAGAA TTCGACGCCG CGCATCGGAA
       GCPS18-129Sam-ba2  GACGAAACTT TCCGATCACC GCCACCAGAA TTCGACGCCG CGCATCGGAA
      GCPR18-3129R211-ba2 GACGAAACTT TCCGATCACC GCCACCAGAA TTCGACGCCG CGCATCGGAA
       GCP18-10129R20-ba2 GACGAAACTT TCCGATCCCC GCC.CCAGAA TTCGACGCCG CGCATCGGAA
              Consensus   gacgaaactt tccgatcacc gccaccagaa ttcgacgccg cgcatcggaa 581                                                              630
         EMBH44836anti    GGATCCGAAT CGGGAACTGG AGTGAACCCG AGCGATCCCG GGAGTGCGAC
      GCP18-5CP418L-Sams  GGATCCGAAT CGGGAACTGG AGTGAACCCG AGCGATCCCG GGAGTGCGAC
       GCP18-2CP418L-Wes  GGATCCGAAT CGGGAACTGG AGTGAACCCG AGCGATCCCG GGAGTGCGAC
     GCP18-4CP418L-R2000  GGATCCGAAT CGGGAACTG. AGTGAACCCG AGCGATCCCG GGAGTGCGAC
         conse129ba1-Drak GGATCCGAAT CGGGAACTGG AGTGAACCCG AGCGATCCCG GGAGTGCGAC
       GCPS18-129Sam-ba2  GGATCCGAAT CGGGAACTGG AGTGAACCAG AGCGATCCCG GGAGTGCGAC
      GCPR18-3129R211-ba2 GGATCCGAAT CGG.AACTGG AGTGAACCAG AGCGATCCCG GGAGTGCGAC
       GCP18-10129R20-ba2 GGATCCGAAT CGGGAACTGG AGTGAACCAG AGCGATCCCG GGAGTGCGAC
              Consensus   ggatccgaat cgggaactgg agtgaacc.g agcgatcccg ggagtgcgac
```

Figure 15 (c)

```
                    631                                                    690
     EMBH44836anti  GGAGCGATGG GAAAAGAGAG TGGCACGATT TCGACGAAGA GTGGAAGAGG
  GCP18-5CP418L-Sams GGAGCGATGG GAAAAGAGAG TGGCACGATT TCGACGAAGA GTGGAAGAGG
   GCP18-2CP418L-Wes GGAGCGATGG GAAAAGAGAG TGGCACGATT TCGACGAAGA GTGGAAGAGG
  GCP18-4CP418L-R2000 GGAGCGATGG GAAAAGAGAG TGGCACGATT TCGACGAAGA GTGGAAGAGG
      conse129bal-Drak GGAGCGATGG GAAAAGAGAG TGGCACGATT TCGACGAA.A GTGGAAGAGG
     GCPS18-129Sam-ba2 GGAGCGTTGG AAAAAGAGAG TGGCACGATT TCGACGAAGA GAGGAAGAGG
    GCPR18-3129R211-ba2 GGAGCGTTGG AAAAAGAGAG TGGCACGATT TCGACGAAGA GAGGAAGAGG
    GCP18-10129R20-ba2 GGAGCGTTGG AAAAAGAGAG TGGCACGATT TCG.CGAAGA GAGGAAGAGG
          Consensus  ggagcg.tgg .aaaagagag tggcacgatt tcgacgaaga g.ggaagagg 691                                                    740
     EMBH44836anti  AGAGGGTGGT GGATAAACTC GCGTATGATC AAGTTCGTCA TCGTCCTGAT
  GCP18-5CP418L-Sams AGAGGGTGGT GGATAAACTC GCGTATGATC AAGTTCGTCA TCGTCCTGAT
   GCP18-2CP418L-Wes AGAGGGTGGT GGATAAACTC GCGTATGATC AAGTTCGTCA TCGTCCTGAT
  GCP18-4CP418L-R2000 AGAGGGTGGT GGATAAACTC GCGTATGATC AAGTTCGTCA TCGTCCTGAT
      conse129bal-Drak AGAGGGTGGT GGATAAACTC GCGTATGATC AAGTTCGTCA TCGTCCTGAT
     GCPS18-129Sam-ba2 AGAGGGTGGT GGATAAACTC GCGTATGATC AAGTTCGTCA TCGTCCTGAT
    GCPR18-3129R211-ba2 AGAGG.TGGT GGATAAACTC GCGTATGATC AAGTTCGTCA TCGTCCTGAA
    GCP18-10129R20-ba2 AGAGGGTGGT GGATAAACTC GCGTATGATC AAGTTCGTCA TCGTCCTGAA
          Consensus  agagggtggt ggataaactc gcgtatgatc aagttcgtca tcgtcctga 741                              pSG129antiU  790        800
     EMBH44836anti  TGCCGCCATT TTTTTTGTCA GGGCGCTCTG TGGCTTAGAA GTTTCCGATG
  GCP18-5CP418L-Sams TGCCGCCATT TTTTTTGTCA GGGCGCTCTG TGGCTTAGAA GTTTCCGATG
   GCP18-2CP418L-Wes TGCCGCCATT TTTTTTGTCA GGGCGCTCTG TGGCTTAGAA GTTTCCGATG
  GCP18-4CP418L-R2000 TGCCGCCATT TTTTTTGTCA GGGCGCTCTG TGGCTTAGAA GTTTCCGTG.
      conse129bal-Drak TGCCGCCATT TTTTTTGTCA GGGCGCTCTG .GGCTTAGAA GTTTCCGA..
     GCPS18-129Sam-ba2 TGCCGCCATT CTTGTTCAC. .GGCGCTCTG GGT....... ..........
    GCPR18-3129R211-ba2 TGCCGCC... .......... .......... .......... ..........
    GCP18-10129R20-ba2 TGCC..CAT. CTTGAGCTC. .GG.GCGCGG GCTCACAA.. ..........
          Consensus  tgccgccat. .tt.....c. .gg.gc.c.g ...,...... ..........

791
     EMBH44836anti  TCAATGAAC A GTGACACGAC GAAATGC
  GCP18-5CP418L-Sams TCAATGAAAC AGAAT...TC CGGG...
   GCP18-2CP418L-Wes CCAATGAACA AGATTATTTC CGATG..
  GCP18-4CP418L-R2000 .......... .......... .......
      conse129bal-Drak .......... .......... .......
```

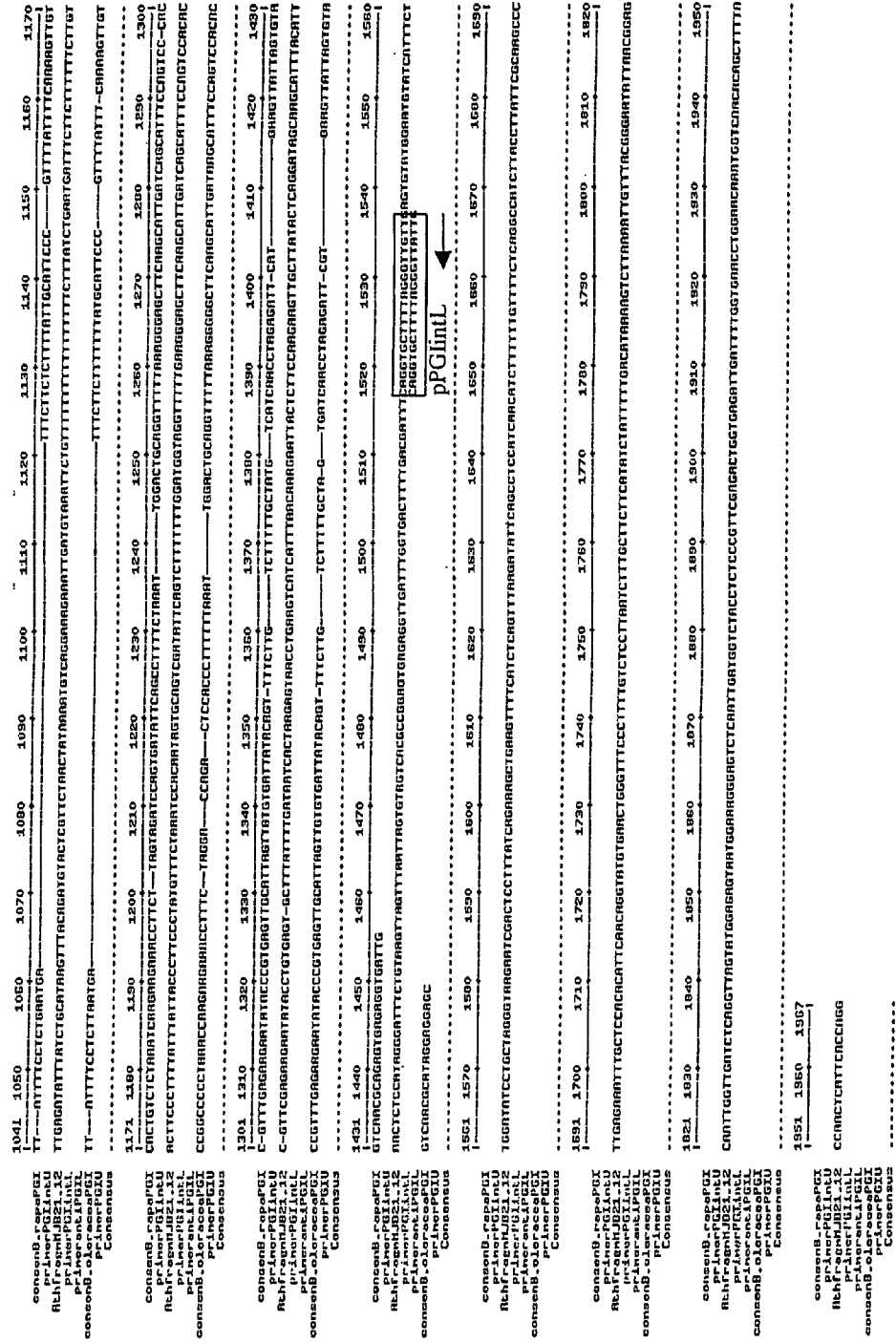
Figure 16 BIS

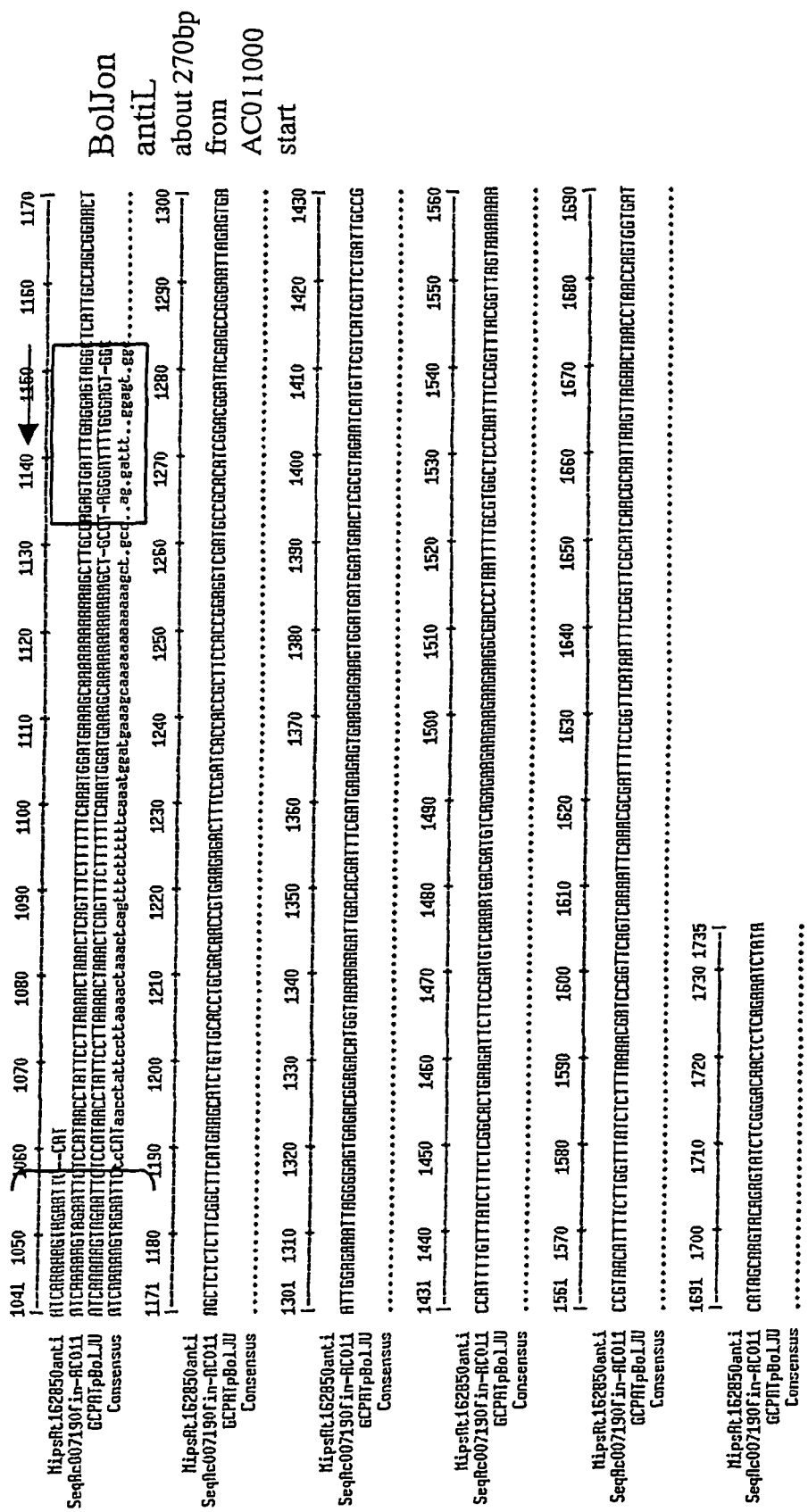
Figure 17 BIS

US 7,812,217 B2

METHOD OF PRODUCING DOUBLE LOW RESTORER LINES OF BRASSICA NAPUS HAVING A GOOD AGRONOMIC VALUE

The present application is a national phase entry under 35 U.S.C. §371 of International Application No. PCT/IB04/02491 filed Jul. 5, 2004, which claims priority under 35 USC 119(d) to European application no. 03293057.0 filed Dec. 8, 2003 and European application no. 03291677.7 filed Jul. 4, 2003, all of which are incorporated herein by reference.

BACKGROUND OF THE INVENTION

Breeding restorer lines for the Ogu-INRA Cytoplasmic Male Sterility (cms) system in rapeseed (*Brassica napus* L.) has been a major objective during the past few years. Extensive backcross and pedigree breeding were necessary to improve their female fertility and to get double low restorer lines. The so-called <<double low >> varieties are those low in erucic acid in the oil and low in glucosinolates in the solid meal remaining after oil extraction. However some difficulties can still be encountered in breeding these lines (introgression rearrangements, possible linkage with negative traits) due to the large size of the radish introgression.

The inventors thus assigned themselves the objective of providing a new improved double low restorer line with a good agronomic value.

This objective is obtained by a new method of producing a recombined double low restorer line for the Ogu-INRA cms in rapeseed.

SUMMARY OF THE INVENTION

A first object of the present invention relates to a method of producing double low restorer lines of *Brassica napus* for Ogura cms presenting radish introgression carrying the Rfo restorer gene deleted of the radish Pgi-2 allele and recombined with the Pgi-2 gene from *Brassica oleracea*, and having a good agronomic value characterised by female fertility, a good transmission rate of Rfo and a high vegetative vigour, said method including the step of:
  a) crossing double low cms lines of spring *Brassica napus* comprising a deleted radish insertion with the double low line of spring Drakkar for forming heterozygous restored plants of *Brassica napus*,
  b) irradiating before meiosis the heterozygous restored plants obtained in step a) with gamma ray irradiation,
  c) crossing pollen from flowers obtained in step b) with the cms double low spring Wesroona line,
  d) testing the progeny for vigour, female fertility and transmission rate of the cms gene,
  e) selecting progeny lines.

In the present invention, the term "lines(s)" means a plant which is essentially homozygote and which is reproducible by auto-pollination.

The above method, wherein the irradiation dose in step b) is 65 Gray during 6 mn.

According to one advantageous form of embodiment of the method according to the present invention, the double low cms line of spring *Brassica napus* of step a) is R211.

R211 is an INRA spring restorer line.

Drakkar is a French spring registered variety.

Wesroona is an Australian spring registered variety.

According to one advantageous form of embodiment of the method according to the present invention, the testing is performed with the combination of five markers selected from PGIol, PGIUNT, PGIint, BolJon and CP418.

Another object of the present invention relates to double low restorer lines of *Brassica napus* for Ogura cms presenting a Rfo insertion deleted of the radish Pgi-2 allele and recombined with the Pgi-2 gene from *Brassica oleracea*, and having a good agronomic value characterised by female fertility, a good transmission rate of Rfo and a high vegetative vigour.

According to one advantageous form of embodiment, the double low restorer lines present a unique combination of five markers selected from PGIol, PGIUNT, PGIint, BolJon and CP418.

Another object of the present invention relates to *Brassica napus* hybrid plants and progeny thereof obtained though the steps of:
  a) providing a restorer line produced according to the above method and bred to be homozygous,
  b) using said restorer line in a hybrid production field as the pollinator,
  c) using cms sterile plants in a hybrid production field as the hybrid seed producing plant, and
  d) harvesting the hybrid seed from the male sterile plant.

Another object of the present invention relates to seeds of *Brassica* plant obtained from the methods according to the present invention.

Still another object of the invention relates to seeds of *Brassica napus* deposited in NCIMB Limited, 23 St Machar Drive, Aberdeen, Scotland, AB24 3RY, UK, on Jul. 4, 2003, under the reference number NCIMB41183.

Another object of the present invention relates to the use of at least four markers PGIol, PGInt, BolJon and CP418, or any portion of them comprising at least one polymorphic site, for characterising recombined restorer lines of *Brassica napus* for Ogura ems presenting a Rfo insertion deleted of the radish Pgi-2 allele and recombined with the Pgi-2 gene from *Brassica oleracea*, and having a good agronomic value characterised by female fertility, a good transmission rate of Rfo and a high vegetative vigour.

In a preferred embodiment, the combination is of five markers PGIol, PGIUNT, PGInt, BolJon and CP418.

In the present invention, the expression "any portion of them comprising at least one polymorphic site" means any part of the sequence showing at least a difference between the *B. oleracea* type sequence and *B. rapa* type sequence.

Such markers are represented in the following figures and sequence listing for the R2000 line.

According to one advantageous form of embodiment, the present invention relates to:
  The marker PGIol which is amplified using the primers:
    PGIol U and PGIol L
    (PGIol U: 5'TCATTTGATTGTTGCGCCTG3' (SEQ ID NO:6);
    PGIol L: 5'TGTACATCAGACCCGGTAGAAAA3' (SEQ ID NO:7))
  The marker PGIint which is amplified using the primers:
    PGIint U and PGIint L
    (PGIint U: 5'CAGCACTAATCTTGCGGTATG3' (SEQ ID NO:8);
    PGIint L: 5'CAATAACCCTAAAAGCACCTG3' (SEQ ID NO:9))
  The marker PGIUNT which is amplified using the primers:
    PGIol U and PGIint L:
    (PGIol U: 5'TCATTTGATTGTTGCGCCTG3' (SEQ ID NO:10);
    PGIint L: 5'CAATAACCCTAAAAGCACCTG3' (SEQ ID NO:11))

The marker BolJon which is amplified using the primers:
BolJon U and BolJon L:
(BolJon U: 5'GATCCGATTCTTCTCCTGTTG3' (SEQ ID NO:12);
BolJon L: 5'GCCTACTCCTCAAATCACTCT3' (SEQ ID NO:13))
The marker CP418 which is amplified using the primers:
SG129 U and pCP418 L:

(SG129 U: cf Giancola et al, 2003 *Theor Appl. Genet.* (*in press*)
pCP418 L: 5'AATTTCTCCATCACAAGGACC3') (SEQ ID NO:14)

Another object of the present invention relates to the PGIo1, PGIUNT, PGIint, BolJon and CP418 markers whose sequences follow:

```
PGIo1 R2000 marker:                                              (SEQ ID NO: 1)
TCATTTGATT GTTGCGCCTG TCGCCTTGTT GTGTTATGAT GAATGAACAG CAGTCATTTA   60

ACATGTGGTT AACTTAACAG GGCTCCGGCT GTTGCAAAAC ACATGGTTGC TGTCAGCACT  120

AATCTTGCGG TATGAATTTG TGATTAAATT TGTTTGTTTG TGACTCTTTC TTCATTGTTC  180

GTTTTCGTAC AATAAACCGA ATGTATAATC TTTTTACAAA CTGAATTTTC TACCGGGTCT  240

GATGTACA                                                          248

PGIUNT R2000 marker:                                             (SEQ ID NO: 2)
TCATTTGATT GTTGCGCCTG TCGCCTTGTT GTGTTATGAT GAATGAACAG CAGTCATTTA   60

ACATGTGGTT AACTTAACAG GGCTCCGGCT GTTGCAAAAC ACATGGTTGC TGTCAGCACT  120

AATCTTGCGG TATGAATTTG TGATTAAATT TGTTTGTTTG TGACTCTTTC TTCATTGTTC  180

GTTTTCGTAC AATAAACCGA ATGTATAATC TTTTTACAAC TGAATTTTCT ACCGGGTCTG  240

ATGTACAATG CTAGTCTCCA TGTTCTTGGG GATCATGATT TATTTTCTAC ATGTATTCAG  300

ACAGTACAGA AGAAAGTGTT CAAAACTCTG GATGTTTTAA TTTACAGTTA GTGGAGAAGT  360

TCGGCATTGA TCCGAACAAT GCATTTGCAT TTTGGGACTG GGTTGGTGGA AGGTACAGTG  420

GTAAGTGCTT GTTTATTTGG TTGTATAAAT TTCTCGTCCA TTTCCGCTTG CTTAGTGTAT  480

AACTGAAATT CTTTTGCAGT TTGCAGTGCT GTTGGAGTCT TACCATTGTC TCTACAGTAT  540

GGCTTCTCTG TGGTTGAGAA GTACGGTACC TTCTACTTTA TCAGCCATCT CATAAAATGT  600

CTTAGGCATA TTCTTTCTAT TTTATTTCCC TCTTAATGAT TTCTTCTTTT TTTTATTGCA  660

TTCCCGTTTT ATTTTCAAAA GTTGTTACTG TCTCTAAATC AAGAAGAAAC CTTCTTAGTA  720

GATCCAGCTG ATATTCAGCC TTTTTTAAAT TGGACTGCAG GTTTTTAAAG GGGAGCTTCA  780

AGCATTGATA AGCATTTCCA GTCCACACCG TTTGAGAAGA ATATACCCGT GAGTTGCATT  840

AGTTGTGTGA TTATACAGTT TTCTTGTCTT TTTGCTATGT CCATCAACAC TAGAGATTCG  900

TGAAGTTATT AGTGTAGTCA ACGCATAGGG AGAGGTGATT GGTGACTTTT GGACGATTTC  960

AGGTGCTTTA GGGTTATTG                                              979

PGIint R2000 marker:                                             (SEQ ID NO: 3)
CAGCACTAAT CTTGCGGTAT GAATTTGTGA TTAAATTTGT TTGTTTGTGA CTCTTTCTTC   60

ATTGTTCGTT TCGTACAAT AAACCGAATG TATAATCTTT TACAAACTGA ATTTTCTACC  120

GGGTCTGATG TACAATGCTA GTCTCCATGT TCTTGGGGAT CATGATTTAT TTTCTACATG  180

TATTCAGACA GTACAGAAGA AAGTGTTCAA AACTCTGGAT GTTTTAATTT ACAGTTAGTG  240

GAGAAGTTCG GCATTGATCC GAACAATGCA TTTGCATTTT GGGACTGGGT TGGTGGAAGG  300

TACAGTGGTA AGTGCTTGTT TATTTGGTTG TATAAATTTC TCGTCCATTT CCGCTTGCTT  360

AGTGTATAAC TGAAATTCTT TTGCAGTTTG CAGTGCTGTT GGAGTCTTAC CATTGTCTCT  420

ACAGTATGGC TTCTCTGTGG TTGAGAAGTA CGGTACCTTC TACTTTATCA GCCATCTCAT  480

AAAATGTCTT AGGCATATTC TTTCTATTTT ATTTCCCTCT AATGATTTC TTCTTTTTTT  540

TATTGCATTC CCGTTTTATT TCAAAAGTT GTTACTGTCT CTAAATCAAG AAGAAACCTT  600

CTTAGTAGAT CCAGCTGATA TTCAGCCTTT TTTAAATTGG ACTGCAGGTT TTTAAAGGGG  660
```

-continued
```
AGCTTCAAGC ATTGATAAGC ATTTCCAGTC CACACCGTTT GAGAAGAATA TACCCGTGAG 720

TTGCATTAGT TGTGTGATTA TACAGTTTTC TTGTCTTTTT GCTATGTCCA TCAACACTAG 780

AGATTCGTGA AGTTATTAGT GTAGTCAACG CATAGGGAGA GGTGATTGGT GACTTTTGGA 840

CGATTTCAGG TGCTTTAGGG TTATTG                                      866

Bo1Jon R2000 marker:                                        (SEQ ID NO: 4)
GATCCGATTC TTCTCCTGTT GAGATCAGCT CCAAACATCA AACAACTTGT ACACAAATAT  60

CTTTACTTGC TAAATGGAAC ATGACAAGAG ATAGAAAATC TTGCTCATAG TATTGTACAA 120

GGGATAACAG TGTAGAAAAC AAACCGTCTG TAAGATTTTC TCCCTGATCC TCTCACTTAA 180

CCAGTAGGCG TTTTTCACAT TGAAGCGCAT ATCTACTTTG GTATTCACTG AATAAAAAAA 240

GAAAGCTGGT AACATGTGAA GGATATACAA GCATTGATAC ACCAAGTAGT CACAAACTAC 300

ATTATAAAGG TCAGACCTTT GTTCACATTC TGGCCTCCAG GACCACCGCT TCTAGCAAAG 360

TTAAGCGTAA CATGGTCTGC ACGTATACAA ATGAAAATGT TTCTATCAAA ATCCTATAAA 420

ATAGAGCTCT ATAACATTGT CGATACATAG TTTCACTAAC TCTGCAAGTA CTAAACACAT 480

ATACAAACAA AACTATGCGA ACAGATCAAA ACTACTACAG AACACAGTTC TATGACACTG 540

TCGATAGTAA CATCCTCTGC AAGTACCAAA GAGATAGCAA ATGAAACTAT GTAAACAAAT 600

CAAAATTCTA AATTTCTCCA TCACAAGGAC CTACAGAATA GAGTTATCAT AACATTTTCT 660

GTAAATATTT CCATCAAAAT GACTAGAGAA CAGAGTTCTT ATAACATTAT CTGTAAATGT 720

TCCAACAAAA CCACTACATA GCAGAGTTCT TATAACATTG TCTGTAAATG TCCAATCAAA 780

ACCACTACAG AACAAAGCTC CTATAACATT GTTTATACAA AGTTTCACTA AATCTACAAA 840

CTTTCCCCGT AAATGAGCTT AATATCACCC AAAGATGTTT CAATCAGATA AAGAGTACGA 900

CATCGTTTTG AGATTAGAAC AAACTGAAAC TTACGTAGAG TGATTTGAGG AGTAGGC    957

CP418L R2000 marker:                                        (SEQ ID NO: 5)
AATTTCTCCA TCACAAGGAC CTACAGAATA GAGTTATCAT AACATTTTCT GTAAATATTT  60

CCATCAAAAT GACTAGAGAA CAGAGTTCTT ATAACATTAT CTGTAAATGT TCCAACAAAA 120

CCACTACATA GCAGAGTTCT TATAACATTG TCTGTAAATG TCCAATCAAA ACCACTACAG 180

AACAAAGCTC CTATAACATT GTTTATACAA AGTTTCACTA AATCTACAAA CTTTCCCCGT 240

AAATGAGCTT AATATCACCC AAAGATGTTT CAATCAGATA AAGAGTAACG ACATCGTTTT 300

GAGATTAGAA CAAACTGAAA CTTACGTAGA GTGATTTGAG GAGTAGGCTC GTTGCCAGCA 360

GAGCTAGCTC TCTCCTCCGC CTCATGAAGC ATCTGTTGCA CCTGAGACAA CCGTGACGAA 420

ACTTTCCGAT CACCGCCACC AGAATTCGAC GCCGCGCATC GGAAGGATCC GAATCGGGAA 480

CTGAGTGAAC CCGAGCGATC CCGGGAGTGC GACGGAGCGA TGGGAAAAGA GAGTGGCACG 540

ATTTCGACGA AGAGTGGAAG AGGAGAGGGT GGTGGATAAA CTCGCGTATG ATCAAGTTCG 600

TCATCGTCCT GATTGCCGCC ATTTTTTTTG TCAGGGCGCT CTGTGGCTTA GAAGTTTCCG 660

ATGTCAATGA AC                                                    672
```

BRIEF DESCRIPTION OF THE DRAWINGS

In the annexed drawing that follows, the following abbreviations are used:
Dra
Drakkar
Rel-15-1, E38, R15
R2000
Hete, He1, R211.Drakkar
heterozygous R211*Drakkar,
Darm
Darmor
Bol:
*Brassica oleracea*
Bra, *B. rap:*
*Brassica rapa*
GCPA18-A19, Wes, Aust:
Wesroona
Sam, Sam1PGIolSunt5
Samourai
RRH1, ba2c RRH1
rav, N.WR
Hybrid *Brassica napus**wild Radish

FIG. 3 illustrates the number of seeds per pod of different lines.

| | |
|---|---|
| PGIol: | primer PGIol U (named in SGAP: BnPGIch 1 U) |
| | primer PGIol L (named in SGAP: Bn PGIch 1 L) |
| PGIint: | primer PGIint U |
| | primer PGIint L (is out side the sequence). |

Figure 5:
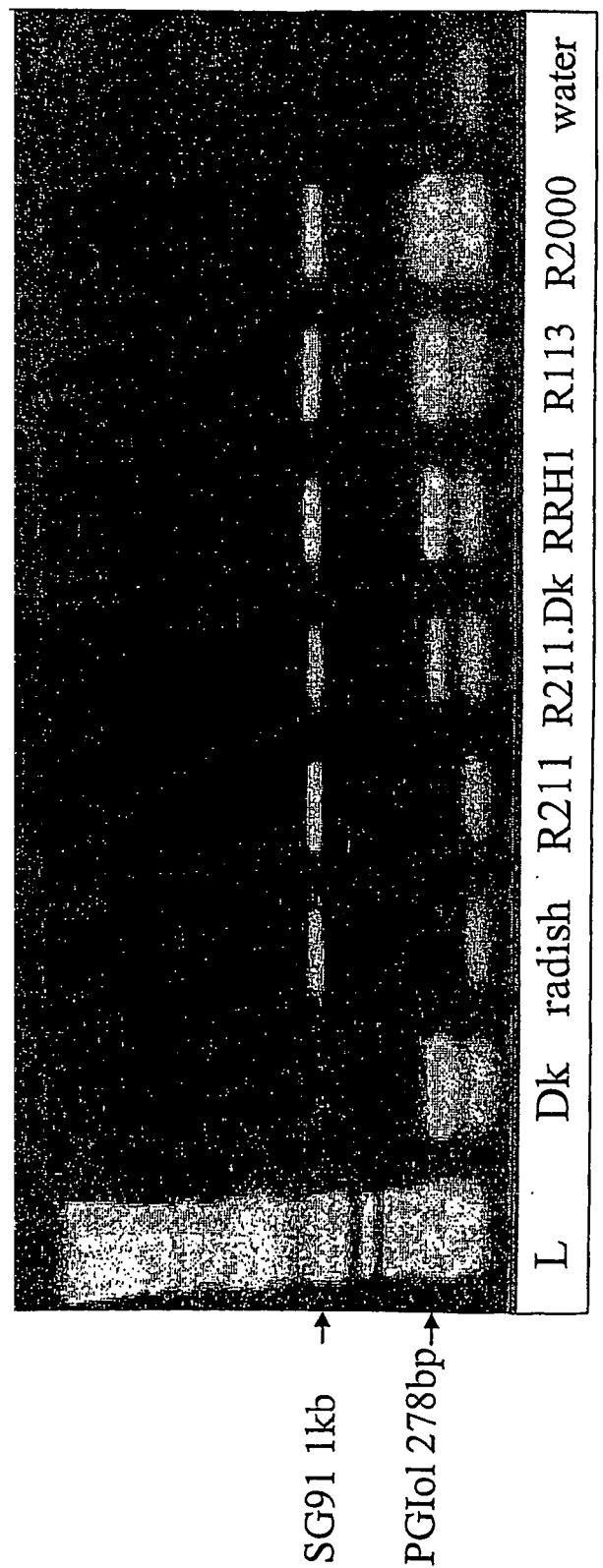

FIG. 5 illustrates electrophoresis gel of PGI-2 gene (PGIol), PCR marker and SG34, a PCR marker close to Rfo.

Figure 6:
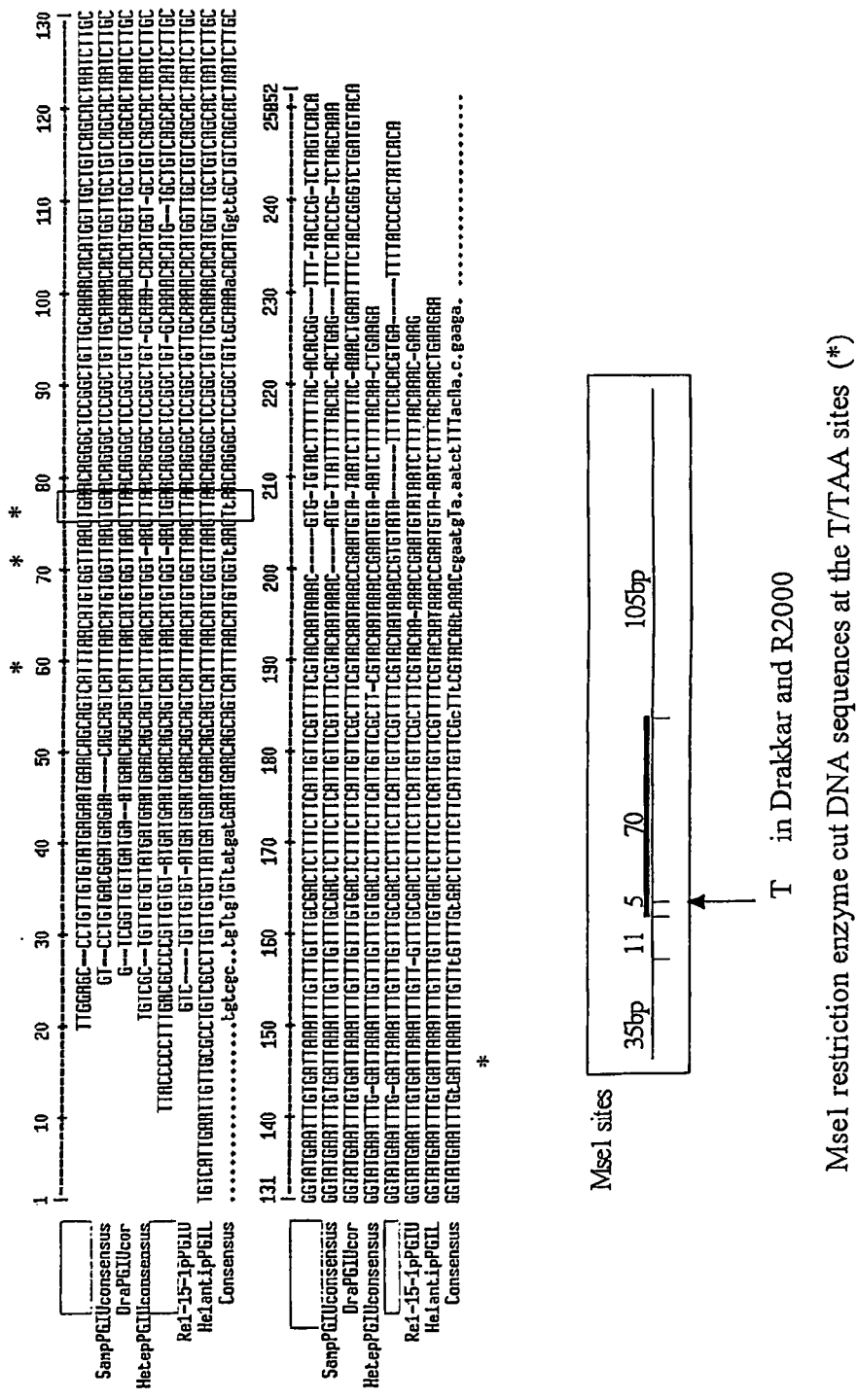

FIG. 6 illustrates Pgi-2 segment of DNA amplified by PCR with PGIol primers.

Figure 7:
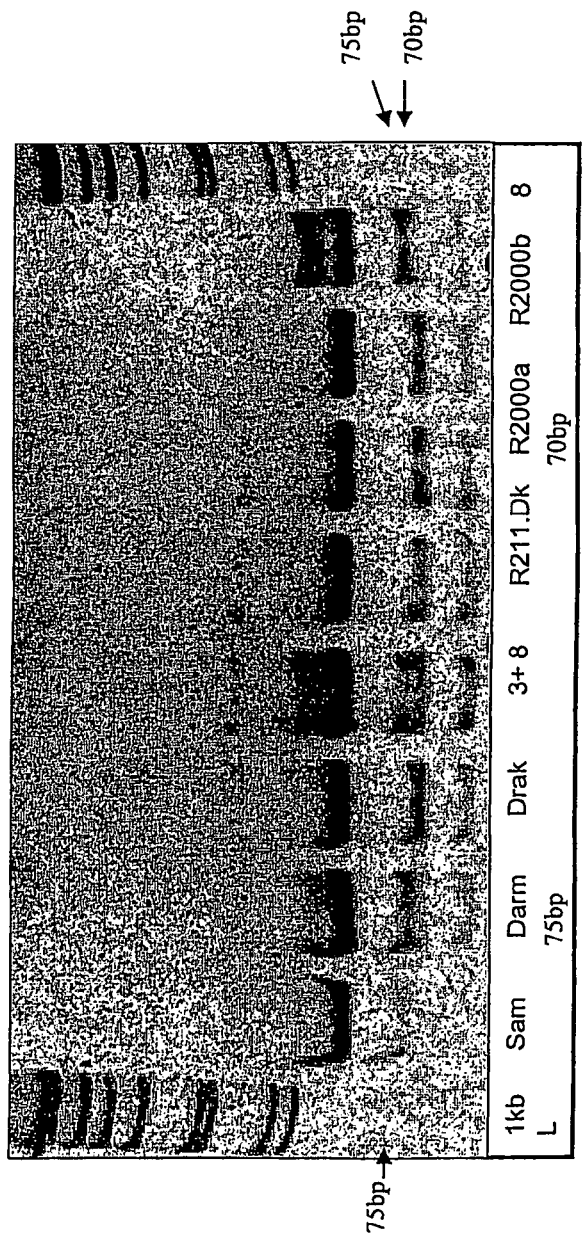

FIG. 7 illustrates digestion of the PCR product PGIol by Mse1.

In that figure:
Sam and Darm has a 75 bp band.
Drak, R211.Dk and R2000 showed a 70 pb one (Acrylamide 15%).
8 was similar to Samourai (75 bp); mix with Drakkar (70 pb) it allowed the visualisation of the two bands.

Figure 8:
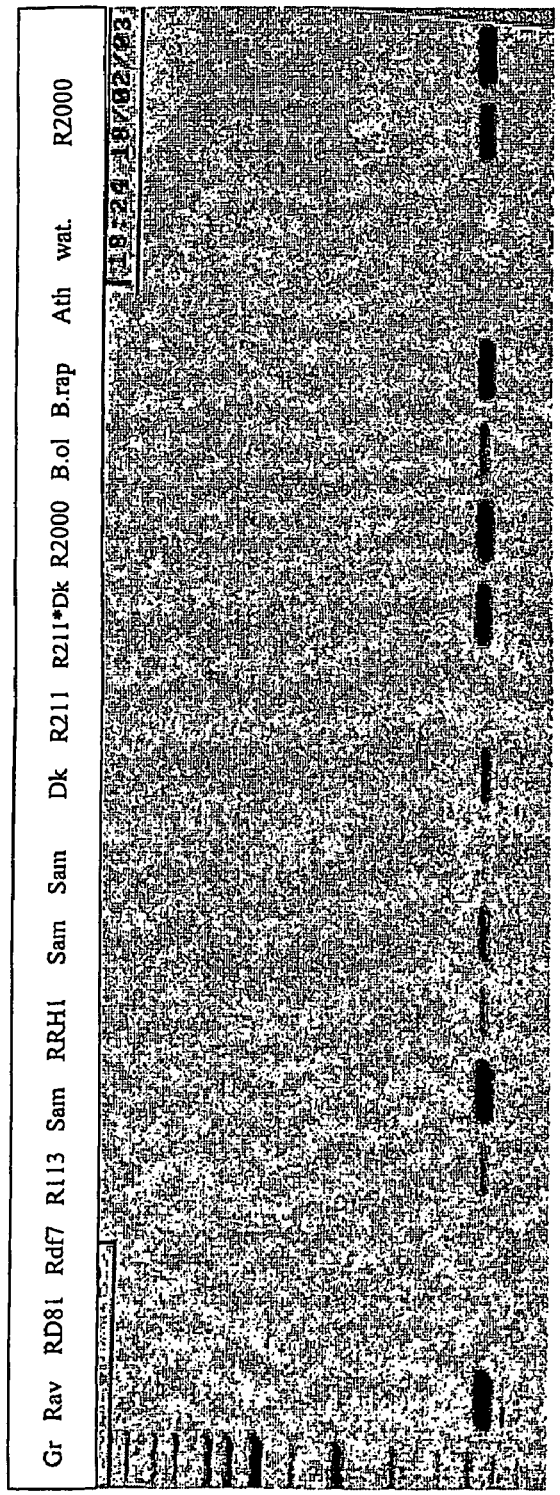

FIG. 8 illustrates electrophoresis agarose gel of PGIUNT marker.

In that figure:
PGIUNT band (about 980 bp) is present in *B. oleracea, B. rapa* cv Asko, maintainer and restored lines except in 'R211'.
There is no amplification in radish and *Arabidopsis*.
In various *Brassica* genotypes only one band was amplified. Size band are similar but sequences are different.

Figure 9:
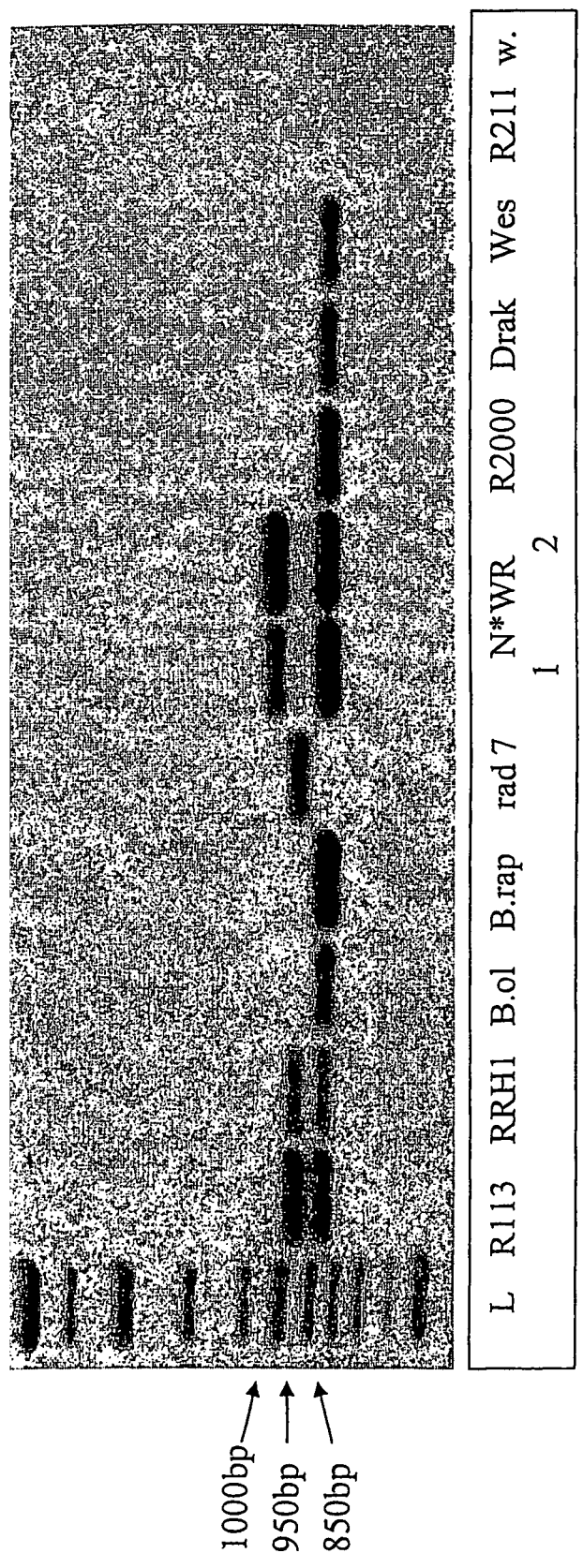

FIG. 9 illustrates electrophoresis gel of PGIint PCR marker.

In that figure PGIint of radish line 7 is of about 950 bp. This band is the same as in the restored RRH1 and R113. It is not found in R211. It is not either in R2000. However the PGIint band is of a similar size of about 870 bp in the various *Brassica* species, but sequences are different.

Figure 10:
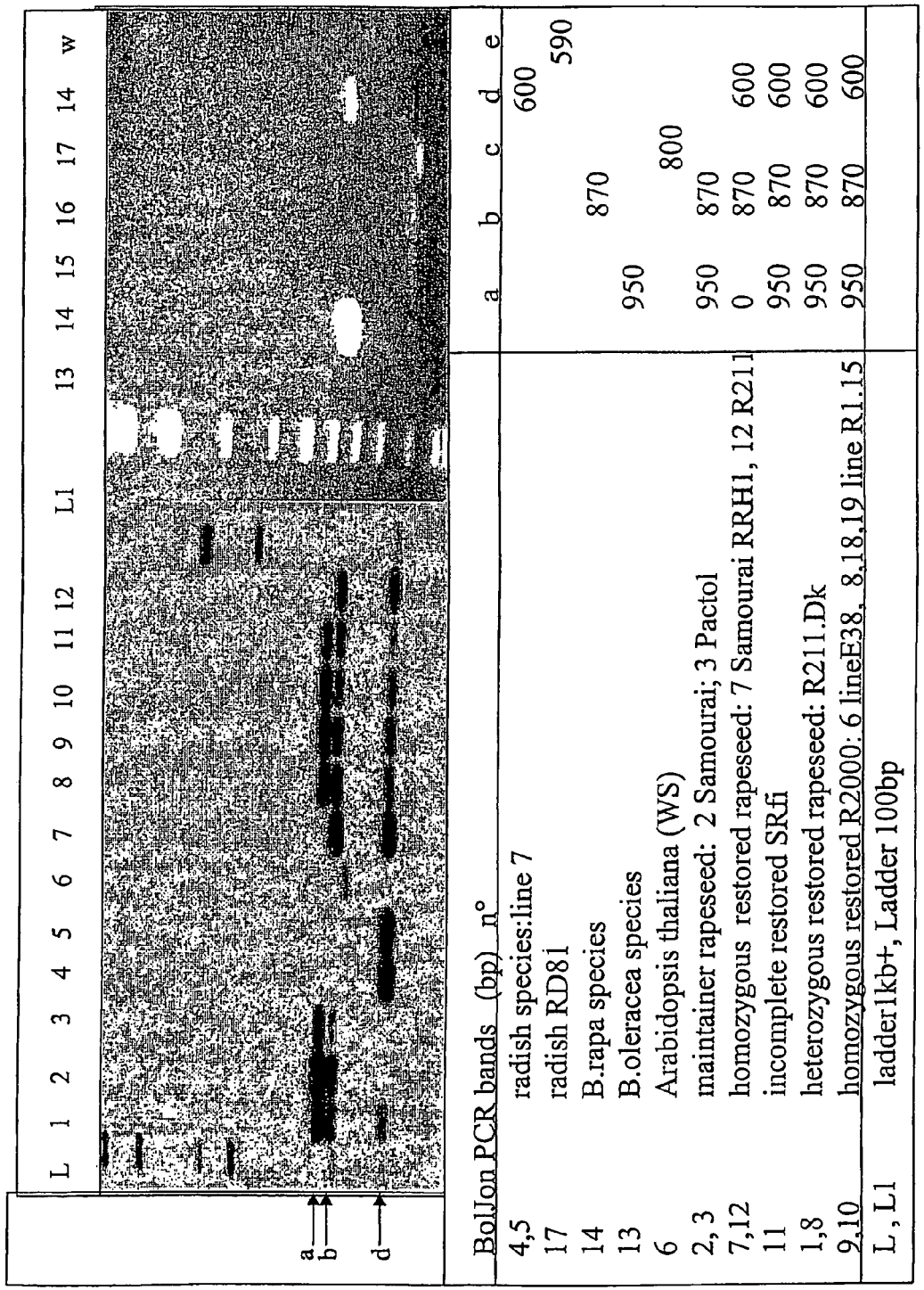

FIG. 10 illustrates electrophoresis agarose gel of BolJon PCR marker.

Figure 11:
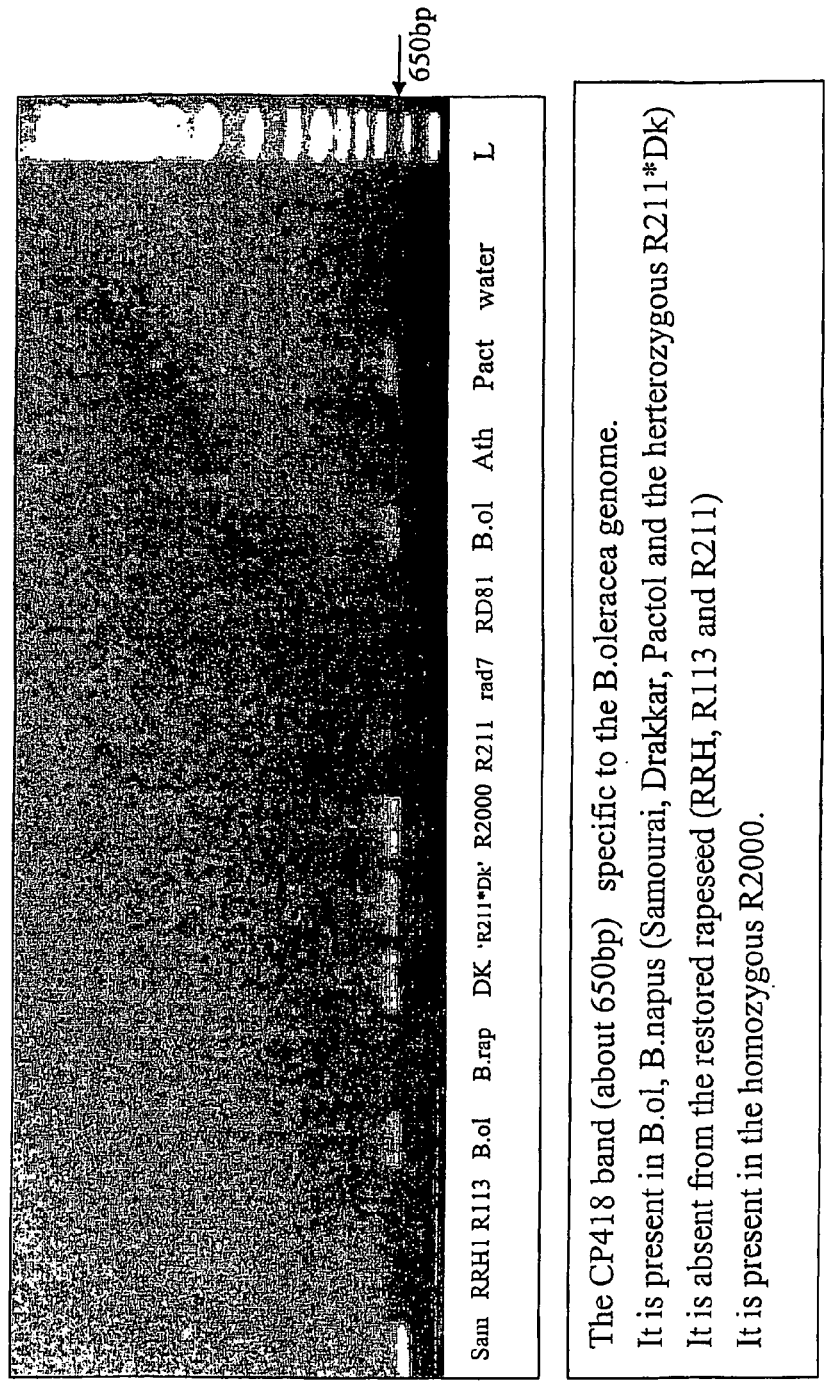

FIG. 11 illustrates electrophoresis agarose gel of CP418 marker.

In that figure, the CP418 band (of about 670 bp) is specific to the *B. oleracea* genome. It is present in *B. ol, B. napus* (Samourai, Drakkar, Pactol and the herterozygous R2111*Dk). It is absent from the restored rapeseed (RRH, R113 and R211). It is present in the homozygous R2000.

Figure 12:
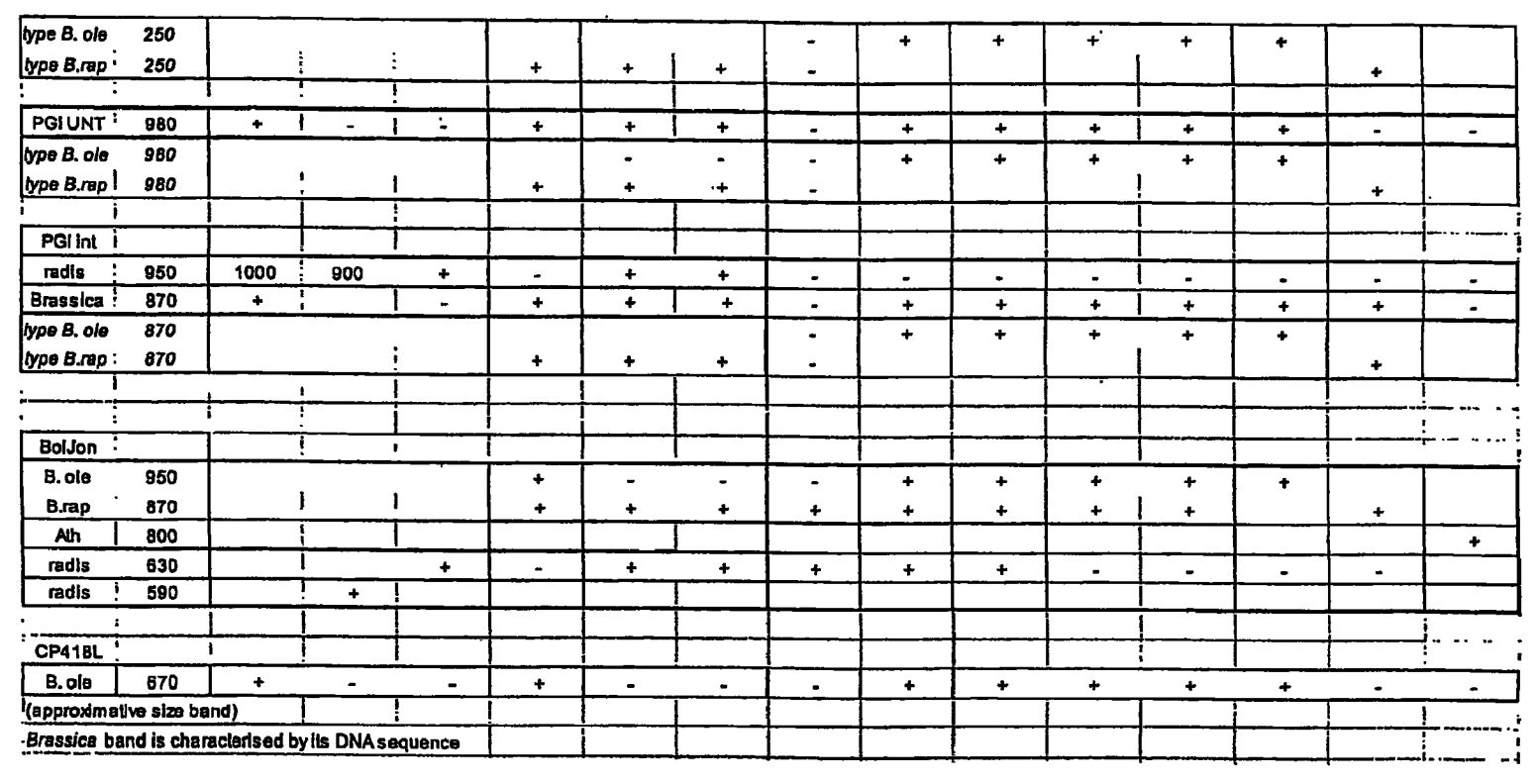

FIG. 12 illustrates summary markers table.

FIG. 13 (13(*a*), 13(*b*)) illustrates PGIol marker sequence alignment between *Arabidopsis*, Radish, *B. rapa, B. oleracea* and R2000.

FIG. 14 (14(*a*), 14(*b*), 14(*c*), 14(*d*)) illustrates the PGIint-UNT marker sequence alignment between *Arabidopsis*, Radish, *B. rapa, B. oleracea* and R2000.

FIG. 15 (15(*a*), 15(*b*), 15(*c*)) illustrates the CP418L marker sequence alignment between *Arabidopsis*, Radish, *B. rapa, B. oleracea* and R2000.

Figure 16:
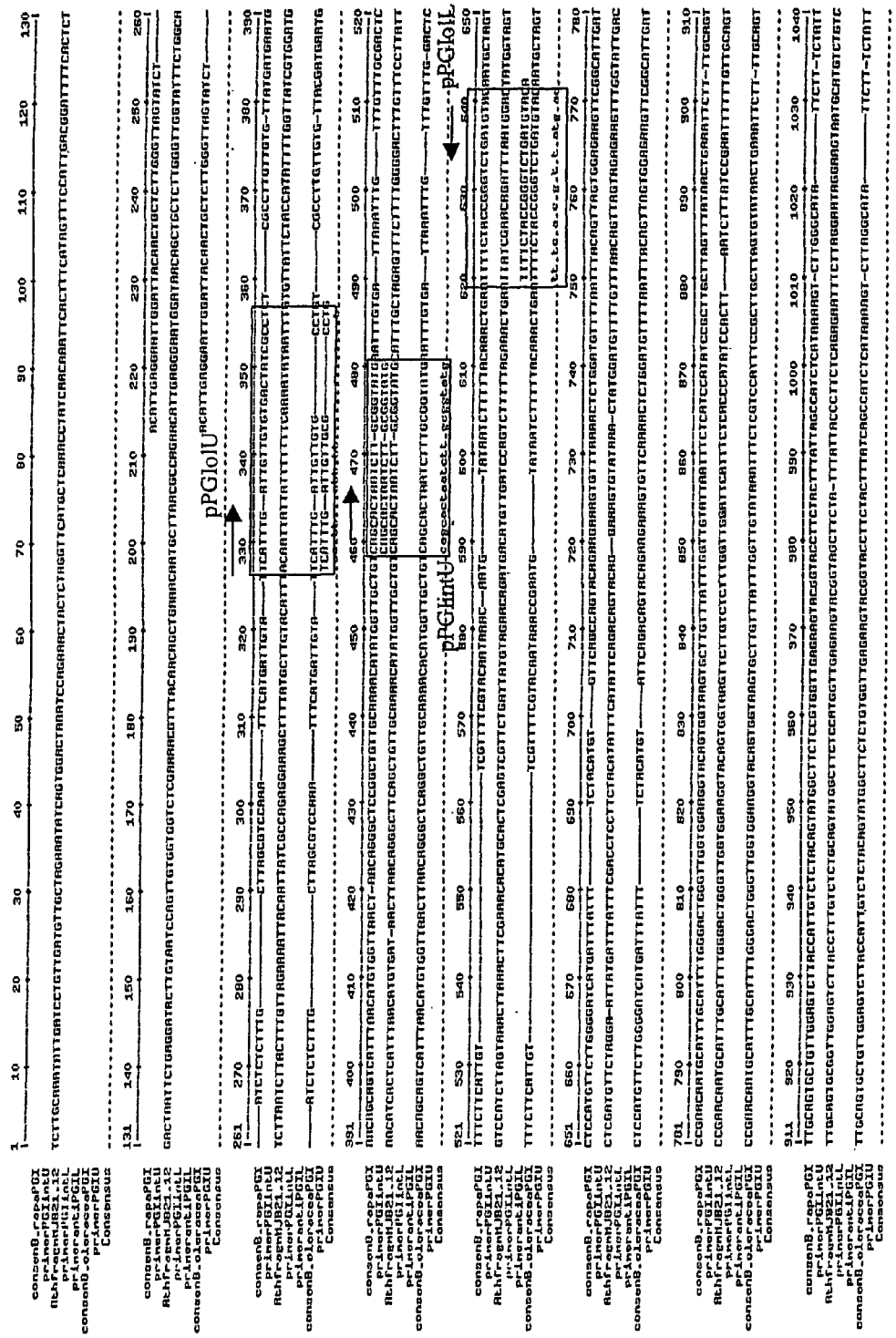

FIG. 16 (16 and 16bis) illustrates *Arabidopsis*, Radish and *B. rapa* BolJon markers. There are aligned with DB sequences of *Arabidopsis* (AC007190end-AC011000beginning), the *B. oleracea* EMBH959102 end and EMBH448336 beginning and representative consensus sequences of the SG129 markers band 1 and 2 in *B. napus* (in Drakkar and Samourai respectively).

From the point 836 bp, AC07190-AC11000 and GCPATp-BOJ sequences are no longer closely homologous to the *Brassica* sequences.

The radish and *B. rapa* (GCPconsen RsRf BOJ and BR) sequences are still closely homologous to the *B. napus* one, from 858 bp point to the 900 bp and 981 points respectively.

In radish, only partial homology is found on the *Brassica* sequence further down.

In *B. rapa* species cv Asko, the left of its BolJon sequence can be aligned again, after a 78 bp deletion, with those of *B. oleracea* and *B. rapa* in *B. napus* from the 1057 bp point to the BolJon L primer.

Figure 17:
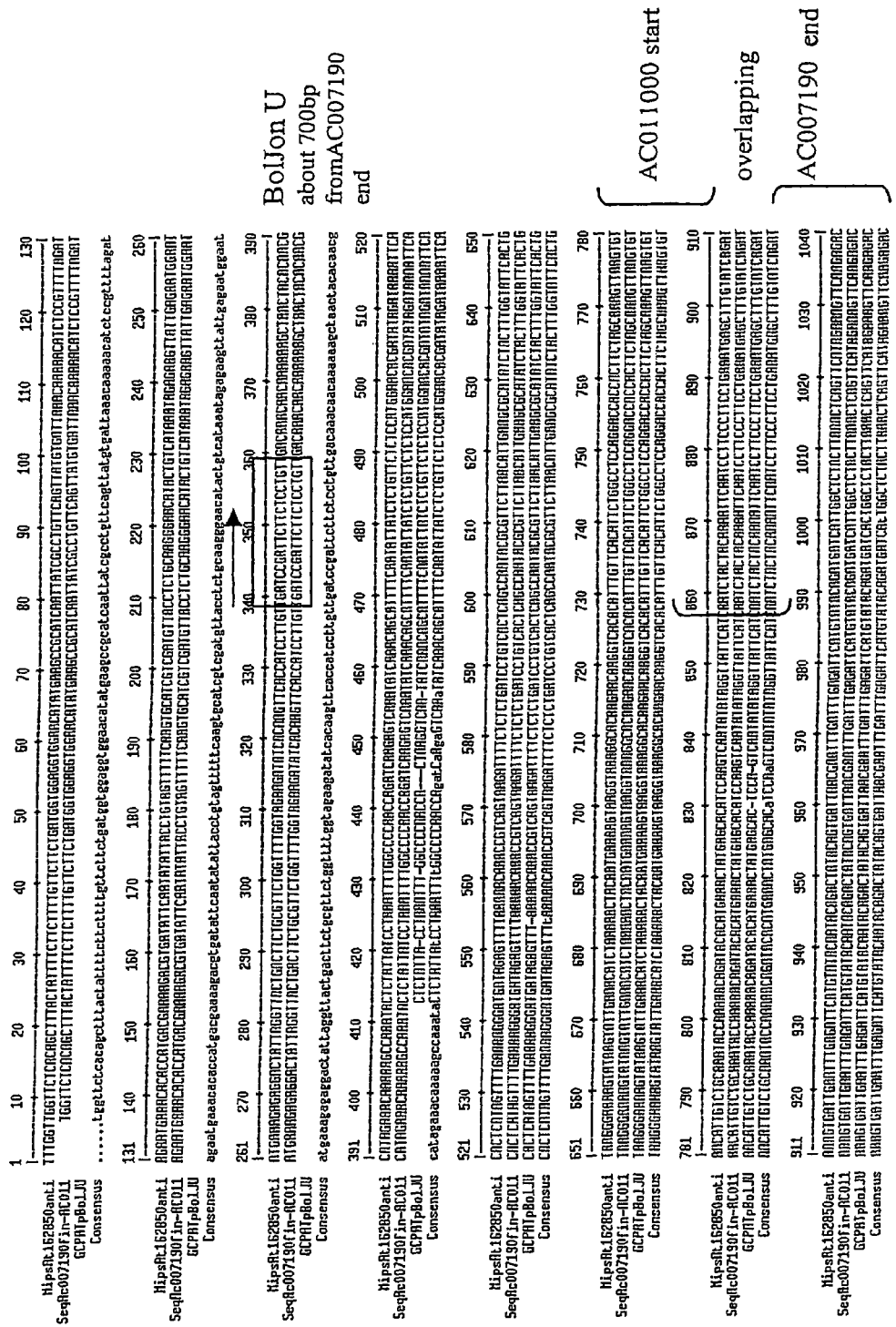

FIG. 17 (17 and 17bis) illustrates the localisation of Pgi-2 primers on the *Arabidopsis th* MJB21.12 sequence.

DETAILED DESCRIPTION OF THE INVENTION

It should be understood, however, that the examples are given solely by way of illustration of the object of the invention, of which they in no way constitute a limitation.

Example I

Method of Producing a Double Low Restorer Line of *Brassica napus* for Ogura Cytoplasmic Male Sterility (cms) Presenting a Radish Introgression, Carrying the Rfo Restorer Gene Deleted of the Radish Pgi-2 Allele and Recombined with the Pgi-2 Gene from *Brassica oleracea*, and Having a Good Agronomic Value Characterised by Female Fertility, a Good Transmission Rate of Rfo and a High Vegetative Vigour Materials and Methods:

Genotypes: The 'R211' line with a deleted radish insertion was crossed to the spring low glucosinolates (GLS) rapeseed 'Drakkar' to produce a F1 progeny ('R211*Dk'). The spring low GLS cms line 'Wesroona' (australian origin) was used for following crosses. The following lines were used as controls in molecular analyses: Winter restored lines derived from 'Samourai' carrying the complete ('RRH1') or incomplete ('R113') introgression as well as European radish line7, Asiatic restored radish D81, hybrid *Brasica napus*, wild radish, *Brassica oleracea*, and *B. rapa* cv Asko, *Arabidopsis thaliana*.

Gamma ray irradiation: Whole flowering plants were treated with gamma rays from a Co60 source in a controlled area. Sublethal dose of 65 Gray was applied before meiosis.

Figure 1:
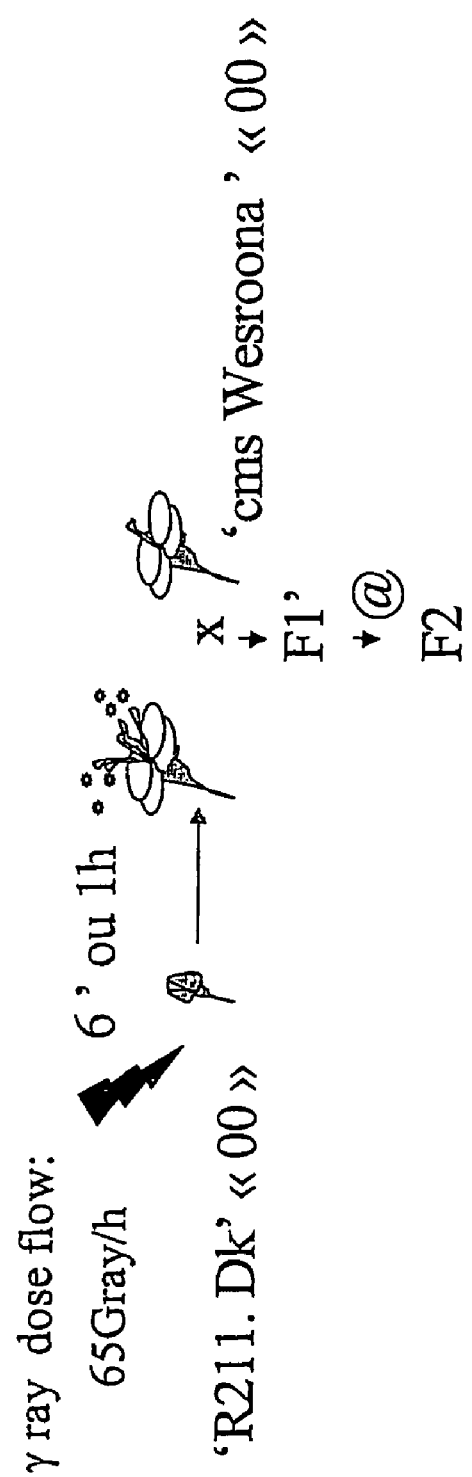
FIG. 1 illustrates Gamma ray Iradiation and F2 production.

Testcrosses and F2 production: Irradiated plants were transferred in an insectproof greenhouse after removing flower buds larger than 2 mm. The irradiated F1 progeny was used to handpollinate the cms 'Wesroona' line. The restored derived F1' plants were allowed to produce F2 families harvested individually and precisely sown in a field assay along with non irradiated controls (FIG. 1).

Phenotypic selection: Three visual criteria were scored (on a 1 to 5 scale) over 2 years in field assays, on 1200 F2 offsprings plus 44 controls (82 330 plants):

1—Vegetative vigour,
2—Normality of the ratio of fertile/sterile plants in the F2 segregation, and
3—Female fertility (pod development and seed set).

Advanced selfed generations of the selected families were obtained either in field or greenhouse and produced homozygous lines (F4) for further analysis.

Isozyme analysis was performed as in (Delourme R. and Eber F. 1992. *Theor Appl Genet* 85: 222-228), marker development from (Fourmann M et al 2002. *Theor Appl. Genet.* 105:1196-1206.): PCR products are validated by sequencing. Alignments were made using Blast Ncbi and Uk Crop Net *Brassica* DB and the Multialin software INRA Toulouse.

Method:

We choose one low GLS spring homozygous restorer line, 'R211', already exhibiting deletions in the introgression (Delourme R. and Eber F. 1992. *Theor Appl Genet* 85: 222-228. Delourme R et al 1998. *Theor Appl Genet* 97: 129-134. Delourme R. et al 1999. 10th *Int. Rapeseed Congress, Canberra.*). Several molecular markers are missing on either side of Rfo, such as spATCHIA (Fourmann M et al 2002. *Theor Appl. Genet.* 105:1196-1206), spSG91 (Giancola S et al 2003 *Theor Appl. Genet. (in press)*). 'R211' lost the isozyme expression of the Pgi-2 allele of the radish gene but also the one of Pgi-2 allele of *B. oleracea* genome (1,2). Moreover, the homozygous 'R211' shows linked negative traits such as low vigour and very poor seed set. We hypothesised that these plants lack a rapeseed chromosomal segment. The fertile ratio in F2 progenies derived from this material is lower than expected (64% instead of 75%). We initiated the program from this 'R211' line and tried to force recombination between the Rfo carrying introgression from this deleted line and the rapeseed homologous chromosome from a double low *B. napus* line.

Ionising irradiation is known to induce chromosomal rearrangements by double strand breaks followed by aberrant rejoining of the ends. Gamma-ray irradiation was used on a heterozygous F1 derived from the 'R211' line to induce chromosome breaks, just before meiosis, aiming at a recombination of the deleted radish introgression in the rapeseed genome.

Results:

Very few families were at the best score for the three criteria out of 1200 F2 families tested.

Figure 2:
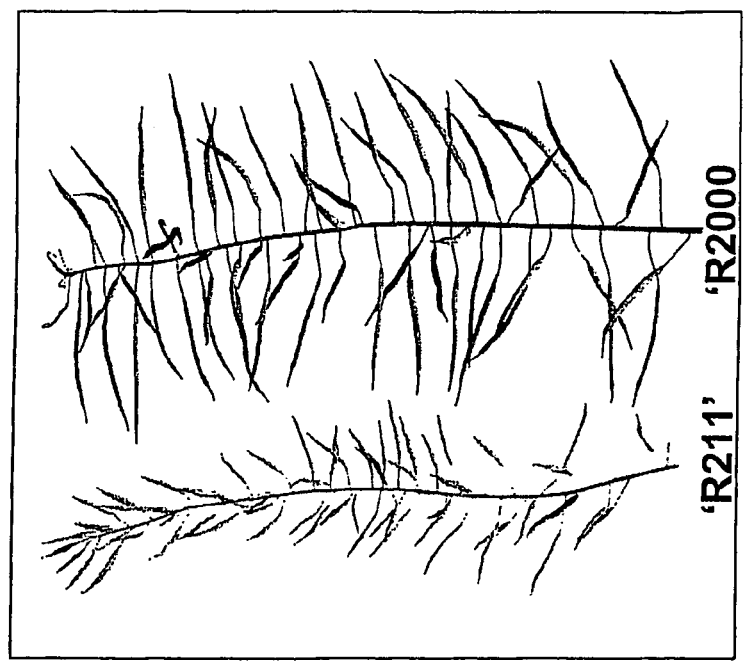
FIG. 2 illustrates seed set on 'R211' and 'R2000'.

Only one, 'R2000', proved to produce a normal ratio of fertile plants per selfed progeny with a stable recovery of good agronomic traits such as a good female fertility, with a normal seed set compared to 'R211' (FIGS. 2 and 3). This family was obtained from a 6 mn irradiation treatment at a dose flow of 65 Gray per hour. Glucosinolate analysis confirmed its low content.

In FIG. 2 (Seed set on 'R211' and 'R2000') R2000 showed normal inflorescences, with a normal looking architecture.

In FIG. 3 (Number of seeds per pod), we observe:
- on the best 'R2000' F4 families in self pollination (Selfings) and in testcrosses
- on 'Pactol' cms line on rapeseed and 'R211' controls.

Example II

Selection of Markers in the Pgi-2 Gene

PGI isoenzyme analysis: 'R2000' progeny expressed the rapeseed Pgi-2 allele from *B. oleracea* genome, originally lost in 'R211'.

Three PCR markers were defined to characterise the R2000 family compared to the known restorer rapeseed RRH1 and R113.

1) PGIol marker was developed from the *Brassica* DB sequences to be specific to the *Brassica* genome. There is no amplification in radish nor in *Arabidopsis th.*, but only in *Brassica*, with one 248 bp band.

2) PGIint marker amplified a longer part of the Pgi-2 gene, allowing clear distinction between the various tested species *Brassica, Raphanus* and *Arabidopsis*. The species *B. rapa* and *B. oleracea* were not distinguished by the band size on agarose gel, but by their PGINT band sequence.

3) PGIUnt marker, a combination of the PGI ol U and PGI int L primers.

This marker had the specificity of the PGIol marker but amplifying a longer part such as PGIint.

II.1 PGIol Marker

Figure 4:
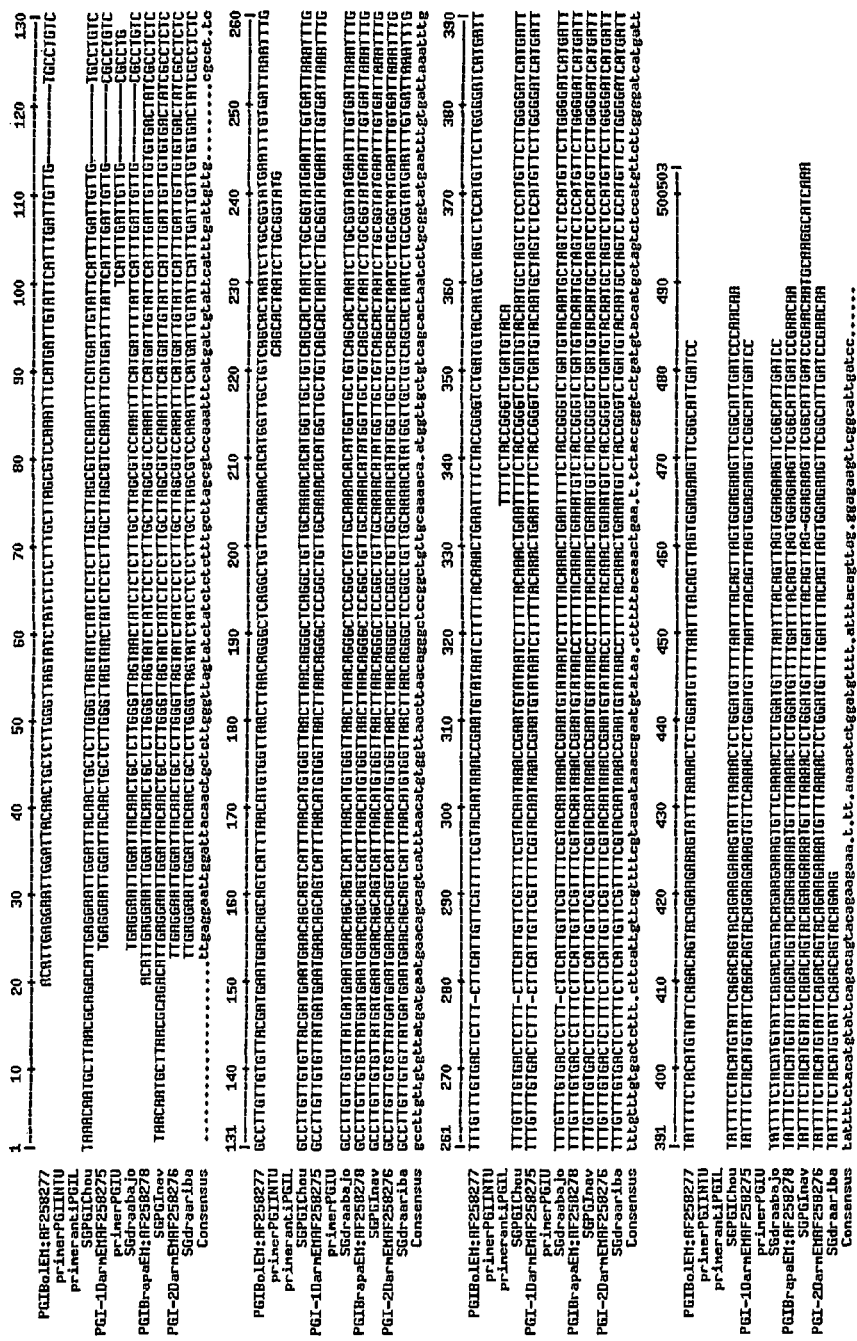
FIG. 4 illustrates PGIol primer localisation on the segment of PGI sequence from Data Base. In that figure.

With the PGIol primers, the 'R211' parental line showed no amplification, while the spring tested lines showed a 248 bp band. Its DNA sequence is homologous to the PGI-2 sequences from the Crop Net UK DB in *Brassica* species and from previous work in our group (named SGAP sequences) (Localisation of the primers SG PGI chou, FIG. 4).

It was ortholog of the clone MJB21-12, on the chromosome V, (34543 bp) in *Arabidopsis* (NCBI DB).

PGIol plus SG34 to set an Homozygocity test:

The combined use of two sets of primers in a mix PCR, PGIol marling the Pgi-2 gene absent in the homozygote restored plant and SG34 (from S. Giancola et al, Giancola S et al 2003 *Theor Appl. Genet. (in press)*), a very close marker to the Rfo gene, was set up to discriminate homozygous from heterozygous plant among the fertile plants segregating in F2 progenies derived from 'R211'. In place of using SG34, it is possible to use any other marker close to or in the Rfo gene.

Only one family R2000 showed no difference between homozygote and heterozygote offsprings:

The Pgi-2 gene is present in the R2000 homozygote, which is not the case for the parental homozygous R211.

In FIG. 5 (PGIol and SG34 PCR markers):

The homozygous 'R2000' family has recovered the PGIol band.

DNA sequence of the band confirmed the homology with the known *Arabidopsis* and *Brassica* Pgi-2 sequence. Control genotypes (Drakkar, Pactol, and, Samourai, Darmor) had the same pattern on the gel. Sequence of this common band allowed to confirm their high homology as they were quasi similar except one base substitution.

The homozygous 'R2000' family has recovered the PGIol band of the *Brassica oleracea* type. It was distinct from the known restorer of the Samourai group.

This amplified part of the Pgi-2 is very conserved and hardly any differences were shown among the various genotypes. A longer part of Pgi-2 gene was investigated.

II.2 PGIUNT and PGIint Markers

Electrophoresis Patterns of PCR Products:

PGIUNT marker: A second reverse primer, PGIint L, was designed further down the Pgi-2 sequence, to amplify as well conserved and as variable regions of the gene. When used with the PGIol U primer, it amplifies a 980 bp band only in *Brassica* genomes.

R211 didn't show any band, The homozygous 'R2000' showed the PGIUNT band as in the Drakkar parent.

In FIG. 8 (PGIUNT Marker):

PGIint marker amplified a segment of PGIUNT. The upper primer PGIint allows the amplification in all tested species, allowing a clear distinction between *Arabidopsis*, Radish and *Brassica*. *B. rapa* and *B. oleracea* were not distinguished by the band size on agarose gel, but by their PGIint sequence. All tested restored genotypes, but the 'R211' line, exhibited the European radish band and one *Brassica* band, homologous to the *B. rapa* one.

The homozygous 'R2000' didn't show the radish PGIint band, as in the deleted 'R211' parental line, but showed one *Brassica* band, homologous to the *B. oleracea* one.

Electrophoresis of PGIint marker is represented in FIG. 9.

Sequence Analysis:

Comparison of the PGI sequences from the data bases.

A PGI segment of about 490 bp is known.

Sequences of a segment of about 490 bp from different genotypes (*B. oleracea, B. rapa, B. napus*) have been studied in our laboratory group and some sequences were given to Brassica Crop Net DB: EMAF25875 to 25788 by M. Fouramnn (4) These sequences are very conserved.

Comparison of the *B. rapa* et *B. oleracea* species PGI sequences (FIGS. 13 and 14): Comparison between PGI sequences we have obtained from the tested genotypes of *B. oleracea* and *B. rapa* species, showed that they were distinct by 21 base substitutions. Theses substitutions allowed to distinguish PGIint sequences from the other tested genotypes of rapeseed, homologous to either *B. rapa* cv Asko (RRH1 and R113) or *B. oleracea* (Drakkar, R211*DK but also R2000).

Example III

Selection of Marker in a Region Close to Rfo

Markers surrounding the Rfo gene in the radish insertion were determined in order to facilitate the Rfo gene cloning (Desloires S et al 2003 *EMBO reports* 4, 6:588-594). One of these, the SG129 PCR marker was located very close to Rfo (Giancola S et al 2003 *Theor Appl. Genet.* (*in press*)): it co-amplified distinct bands in *B. oleracea* and *B. rapa* genomes of *B. napus*, but the radish band was very difficult to see on an agarose gel.

The target SG129 sequence was ortholog of a clone (ACO11000, at the locus F16P17) in *Arabidopsis thaliana*. This clone overlapped an *Arabidopsis* adjacent contig clone (AC07190).

From the *Brassica* Crop Net DB, we found one *B. oleracea* clone, (EMBH448336, 764 bp) blasting with the beginning of the A011000, and a second *B. oleracea* clone (EMBH53971), distant from about 300 bp on the *Arabidopsis* map, that blasted with the end of ACO7190.

We designed a new PCR marker, BolJon, between the two *B. oleracea* clones. We verified that it allowed amplification of a specific PCR bands in the different genotypes compared here.

In FIG. 16 (electrophoresis gel of BolJon PCR products):
In *Arabidopsis*, a BolJon 815 bp band was amplified, homologue to the overlapping segment of the contigs.
In *Brassiceae* diploid species, BolJon marker showed distinct bands: one of 950 bp in *B. oleracea* and one of 870 bp in *B. rapa*. It showed that the two *B. oleracea* clones (EMBH53971 and EMBH448336) are in sequence continuity in *Brassica* genome as it is for the ortholog sequences in *Arabidopsis*.
In *B. napus*, these two bands are co-amplified in the maintainer lines, Samourai or Drakkar.
In radish line7, one BolJon band was amplified of about 630 bp long. The band of the restored radish cmsRd81 was slightly smaller.
In all the restored rapeseed lines, one of the BolJon bands was of the same size as the radish line7. BolJon is a marker of the radish introgression.

The homozygous restored rapeseed lines, 'RRH1', 'R113' and also 'R211', only showed the *B. rapa* band and the 630 bp radish band bp suggesting the *B. oleracea* ortholog of the target gene is absent or has been modified when the radish segment of chromosome was inserted into the rapeseed *B. oleracea* constitutive genome.

'R2000' homozygote plants showed radish PCR BolJon, plus the two *Brassica* BolJon bands, again having recovered the *B. oleracea* one, lost in 'R211' and other restorer lines.

We designed a primer, pCP418L, specific of the *B. oleracea* genome in the tested species. With the SG129U primer it amplified only one PCR band (670 bp) in the *B. oleracea* species. (FIG. 17).

There was no amplification in *B. rapa*, in radish, nor in *Arabidopsis*, but there was a clear CP418 band in *B. napus* maintainer lines. Its sequence was strictly homologous to the EMBH448336 sequence. This marker was in a very conserved DNA sequence allowing no polymorphism between genotypes except by presence/absence.

In RRH1, R113 and in R211 there was no CP418 band, indicating as previously that the *B. oleracea* ortholog of the target gene is absent or has been modified following the radish insertion.

'R2000' homozygote plants showed CP418 band, again having recovered the specific *B. oleracea* one.

In the present invention, a new recombined low GLS restorer line has been selected with a good female fertility. The poor value of line 'R211' allowed selection in the field for a rare recombination event and characterisation the 'R2000' family.

The homozygous 'R2000' presents a unique combination of the PGIol, PGIUNT, PGIint and BolJon markers when compared with the rapeseed restorer analysed yet: PGIinT marker showed that the homozygous restored rapeseed lines, RRH1 and R113 presented the European radish band plus one *Brassica* band, homologous to *B. rapa* genome. 'R2000' shows no radish band, lost as in its parental deleted line R211, but showed one *Brassica* band homologous to *B. oleracea*. The ortholog PGIint sequence in its *B. rapa* genome is not amplified with this marker in R211 and Drakkar genetic background.

PGIol marker and PGIUNT marker sequences in restored lines RRH1 and R 113 were homologous to the *B. rapa* cv Asko one. In 'R2000', PGIUNT sequence is homologous to *B. oleracea*. The ortholog PGIUnt sequence in its *B. rapa* genome is not amplified with this marker in R211 and Drakkar genetic background.

BolJon marker showed that the homozygous restored rapeseed lines, including 'R211' presented the European radish band plus only the *B. rapa* one. 'R2000' shows the two bands of 'R211' plus the recovered *B. oleracea* BolJon band.

CP418 marker showed that 'R2000' recovered this conserved *B. oleracea* segment.

Our hypothesis is that a recombination event took place in the pollen mother cell which gave rise to 'R2000' plants. The deleted radish introgression was then integrated to the normal homologous chromosome segment, carrying the *B. oleracea* type Pgi-2 gene and BolJon target sequence, characterised by these markers, probably from the Drakkar '00' genome present in the irradiated heterozygous 'R211*DK'.

The pattern observed for BolJon suggests that the recombination event resulted in a particular duplicated region, one from radish and one *B. oleracea*, in the 'R2000' family.

The invention claimed is:

1. A method for characterising recombined restorer lines of *Brassica napus* for Ogura cms presenting a Rfo insertion deleted of the radish Pgi-2 allele and recombined with the Pgi-2 gene from *Brassica oleracea*, and having an agronomic value characterised by female fertility, transmission rate of Rfo and vegetative vigour, comprising a step wherein the presence of the five markers PGIol, PGIUNT, PGIint, BolJon and CP418 is detected in said recombined restorer lines and wherein said markers comprise the following sequences:
PGIol marker: SEQ ID NO:1;
PGIUNT marker: SEQ ID NO:2;
PGIint marker: SEQ ID NO:3;
BolJon marker: SEQ ID NO:4; and
CP418 marker: SEQ ID NO:5.

* * * * *

SEQUENCE LISTING

<160> NUMBER OF SEQ ID NOS: 14

<210> SEQ ID NO 1
<211> LENGTH: 248
<212> TYPE: DNA
<213> ORGANISM: Brassica napus
<220> FEATURE:
<223> OTHER INFORMATION: PGIo1 marker

<400> SEQUENCE: 1

```
tcatttgatt gttgcgcctg tcgccttgtt gtgttatgat gaatgaacag cagtcattta    60
acatgtggtt aacttaacag ggctccggct gttgcaaaac acatggttgc tgtcagcact   120
aatcttgcgg tatgaatttg tgattaaatt tgtttgtttg tgactctttc ttcattgttc   180
gttttcgtac aataaaccga atgtataatc tttttacaaa ctgaattttc taccgggtct   240
gatgtaca                                                           248
```

<210> SEQ ID NO 2
<211> LENGTH: 979
<212> TYPE: DNA
<213> ORGANISM: Brassica napus
<220> FEATURE:
<223> OTHER INFORMATION: PGI-UNT R2000 marker

<400> SEQUENCE: 2

```
tcatttgatt gttgcgcctg tcgccttgtt gtgttatgat gaatgaacag cagtcattta    60
acatgtggtt aacttaacag ggctccggct gttgcaaaac acatggttgc tgtcagcact   120
aatcttgcgg tatgaatttg tgattaaatt tgtttgtttg tgactctttc ttcattgttc   180
gttttcgtac aataaaccga atgtataatc tttttacaaa ctgaattttc taccgggtct   240
atgtacaatg ctagtctcca tgttcttggg gatcatgatt tattttctac atgtattcag   300
acagtacaga agaaagtgtt caaaactctg gatgttttaa tttacagtta gtggagaagt   360
tcggcattga tccgaacaat gcatttgcat tttgggactg ggttggtgga aggtacagtg   420
gtaagtgctt gtttatttgg ttgtataaat ttctcgtcca tttccgcttg cttagtgtat   480
aactgaaatt cttttgcagt ttgcagtgct gttggagtct taccattgtc tctacagtat   540
ggcttctctg tggttgagaa gtacggtacc ttctacttta tcagccatct cataaaatgt   600
cttaggcata ttcttttctat tttatttccc tcttaatgat ttcttctttt ttttattgca   660
ttcccgtttt attttcaaaa gttgttactg tctctaaatc aagaagaaac cttcttagta   720
gatccagctg atattcagcc ttttttaaat tggactgcag gttttaaag gggagcttca   780
agcattgata agcatttcca gtccacaccg tttgagaaga atatacccgt gagttgcatt   840
agttgtgtga ttatacagtt ttcttgtctt tttgctatgt ccatcaacac tagagattcg   900
tgaagttatt agtgtagtca acgcataggg agaggtgatt ggtgactttt ggacgatttc   960
aggtgcttta gggttattg                                               979
```

<210> SEQ ID NO 3
<211> LENGTH: 866
<212> TYPE: DNA
<213> ORGANISM: Brassica napus
<220> FEATURE:
<223> OTHER INFORMATION: PGI-int R2000 marker

<400> SEQUENCE: 3

```
cagcactaat cttgcggtat gaatttgtga ttaaatttgt tgtttgtga ctctttcttc    60
```

```
attgttcgtt ttcgtacaat aaaccgaatg tataatcttt tacaaactga attttctacc      120
gggtctgatg tacaatgcta gtctccatgt tcttggggat catgatttat tttctacatg      180
tattcagaca gtacagaaga aagtgttcaa aactctggat gttttaattt acagttagtg      240
gagaagttcg gcattgatcc gaacaatgca tttgcatttt gggactgggt tggtggaagg      300
tacagtggta agtgcttgtt tatttggttg tataaatttc tcgtccattt ccgcttgctt      360
agtgtataac tgaaattctt ttgcagtttg cagtgctgtt ggagtcttac cattgtctct      420
acagtatggc ttctctgtgg ttgagaagta cggtacctcc tactttatca gccatctcat      480
aaaatgtctt aggcatattc tttctatttt atttccctct taatgatttc ttcttttttt      540
tattgcattc ccgttttatt ttcaaaagtt gttactgtct ctaaatcaag aagaaacctt      600
cttagtagat ccagctgata ttcagccttt tttaaattgg actgcaggtt tttaaagggg      660
agcttcaagc attgataagc atttccagtc cacaccgttt gagaagaata tacccgtgag      720
ttgcattagt tgtgtgatta tacagttttc ttgtcttttt gctatgtcca tcaacactag      780
agattcgtga agttattagt gtagtcaacg catagggaga ggtgattggt gacttttgga      840
cgatttcagg tgctttaggg ttattg                                         866

<210> SEQ ID NO 4
<211> LENGTH: 957
<212> TYPE: DNA
<213> ORGANISM: Brassica napus
<220> FEATURE:
<223> OTHER INFORMATION: BoJon marker R2000

<400> SEQUENCE: 4
gatccgattc ttctcctgtt gagatcagct ccaaacatca acaacttgt acacaaatat        60 ctttacttgc taaatggaac atgacaagag atagaaaatc ttgctcatag tattgtacaa      120
gggataacag tgtagaaaac aaaccgtctg taagattttc tccctgatcc tctcacttaa      180
ccagtaggcg ttttttcacat tgaagcgcat atctactttg gtattcactg aataaaaaaa      240
gaaagctggt aacatgtgaa ggatatacaa gcattgatac accaagtagt cacaaactac      300
attataaagg tcagaccttt gttcacattc tggcctccag gaccaccgct tctagcaaag      360
ttaagcgtaa catggtctgc acgtatacaa atgaaaatgt ttctatcaaa atcctataaa      420
atagagctct ataacattgt cgatacatag tttcactaac tctgcaagta ctaaacacat      480
atacaaacaa aactatgcga acagatcaaa actactacag aacacagttc tatgacactg      540
tcgatagtaa catcctctgc aagtaccaaa gagatagcaa atgaaactat gtaaacaaat      600
caaaattcta aatttctcca tcacaaggac ctacagaata gagttatcat aacatttcct      660
gtaaatattt ccatcaaaat gactagagaa cagagttctt ataacattat ctgtaaatgt      720
tccaacaaaa ccactacata gcagagttct tataacattg tctgtaaatg tccaatcaaa      780
accactacag aacaaagctc ctataacatt gtttatacaa agtttcacta aatctacaaa      840
ctttccccgt aaatgagctt aatatcaccc aaagatgttt caatcagata aagagtacga      900
catcgttttg agattagaac aaactgaaac ttacgtagag tgatttgagg agtaggc        957

<210> SEQ ID NO 5
<211> LENGTH: 672
<212> TYPE: DNA
<213> ORGANISM: Brassica napus
<220> FEATURE:
<223> OTHER INFORMATION: CP418L marker R2000
```

-continued

```
<400> SEQUENCE: 5
aatttctcca tcacaaggac ctacagaata gagttatcat aacatttctt gtaaatattt      60
ccatcaaaat gactagagaa cagagttctt ataacattat ctgtaaatgt tccaacaaaa     120
ccactacata gcagagttct tataacattg tctgtaaatg tccaatcaaa accactacag     180
aacaaagctc ctataacatt gtttatacaa agtttcacta aatctacaaa ctttccccgt     240
aaatgagctt aatatcaccc aaagatgttt caatcagata aagagtaacg acatcgtttt     300
gagattagaa caaactgaaa cttacgtaga gtgatttgag gagtaggctc gttgccagca     360
gagctagctc tctcctccgc ctcatgaagc atctgttgca cctgagacaa ccgtgacgaa     420
actttccgat caccgccacc agaattcgac gccgcgcatc ggaaggatcc gaatcgggaa     480
ctgagtgaac ccgagcgatc ccgggagtgc gacggagcga tgggaaaaga gagtggcacg     540
atttcgacga agagtggaag aggagagggt ggtggataaa ctcgcgtatg atcaagttcg     600
tcatcgtcct gattgccgcc atttttttg tcagggcgct ctgtggctta gaagtttccg     660
atgtcaatga ac                                                        672

<210> SEQ ID NO 6
<211> LENGTH: 20
<212> TYPE: DNA
<213> ORGANISM: artificial sequence
<220> FEATURE:
<223> OTHER INFORMATION: PGIol U primer

<400> SEQUENCE: 6
tcatttgatt gttgcgcctg                                                 20

<210> SEQ ID NO 7
<211> LENGTH: 23
<212> TYPE: DNA
<213> ORGANISM: artificial sequence
<220> FEATURE:
<223> OTHER INFORMATION: PGIol L primer

<400> SEQUENCE: 7
tgtacatcag acccggtaga aaa                                             23

<210> SEQ ID NO 8
<211> LENGTH: 21
<212> TYPE: DNA
<213> ORGANISM: artificial sequence
<220> FEATURE:
<223> OTHER INFORMATION: PGIint U primer

<400> SEQUENCE: 8
cagcactaat cttgcggtat g                                               21

<210> SEQ ID NO 9
<211> LENGTH: 21
<212> TYPE: DNA
<213> ORGANISM: artificial sequence
<220> FEATURE:
<223> OTHER INFORMATION: PGIint L primer

<400> SEQUENCE: 9
caataaccct aaaagcacct g                                               21

<210> SEQ ID NO 10
<211> LENGTH: 20
<212> TYPE: DNA
<213> ORGANISM: artificial sequence
```

```
<220> FEATURE:
<223> OTHER INFORMATION: PGIo1 U primer

<400> SEQUENCE: 10
tcatttgatt gttgcgcctg                                               20

<210> SEQ ID NO 11
<211> LENGTH: 21
<212> TYPE: DNA
<213> ORGANISM: artificial sequence
<220> FEATURE:
<223> OTHER INFORMATION: PGIint L primer

<400> SEQUENCE: 11
caataaccct aaaagcacct g                                             21

<210> SEQ ID NO 12
<211> LENGTH: 21
<212> TYPE: DNA
<213> ORGANISM: artificial sequence
<220> FEATURE:
<223> OTHER INFORMATION: BolJon U primer

<400> SEQUENCE: 12
gatccgattc ttctcctgtt g                                             21

<210> SEQ ID NO 13
<211> LENGTH: 21
<212> TYPE: DNA
<213> ORGANISM: artificial sequence
<220> FEATURE:
<223> OTHER INFORMATION: BolJon L primer

<400> SEQUENCE: 13
gcctactcct caaatcactc t                                             21

<210> SEQ ID NO 14
<211> LENGTH: 21
<212> TYPE: DNA
<213> ORGANISM: artificial sequence
<220> FEATURE:
<223> OTHER INFORMATION: pCP418 L primer

<400> SEQUENCE: 14
aatttctcca tcacaaggac c                                             21
```